(12) United States Patent
Vieites Fernandez et al.

(10) Patent No.: US 8,637,297 B2
(45) Date of Patent: Jan. 28, 2014

(54) ISOLATION, IDENTIFICATION AND CHARACTERIZATION OF STRAINS WITH PROBIOTIC ACTIVITY, FROM FAECES OF INFANTS FED EXCLUSIVELY WITH BREAST MILK

(75) Inventors: Jose Maria Vieites Fernandez, Granada (ES); Sergio Munoz Quezada, Granada (ES); Inmaculada Llamas Company, Granada (ES); Jose Maldonado Lozano, Granada (ES); Fernando Romero Braquehais, Alcantarilla (ES); Antonio Francisco Suarez Garcia, Granada (ES); Angel Gil Hernandez, Granada (ES); Carolina Gomez Llorente, Alcantarilla Murcia (ES); Miriam Bermudez Brito, Alcantarilla Murcia (ES)

(73) Assignee: Hero AG, Lenzburg (CH)

( * ) Notice: Subject to any disclaimer, the term of this patent is extended or adjusted under 35 U.S.C. 154(b) by 0 days.

(21) Appl. No.: 13/255,842

(22) PCT Filed: Mar. 9, 2010

(86) PCT No.: PCT/ES2010/000097
§ 371 (c)(1),
(2), (4) Date: Nov. 22, 2011

(87) PCT Pub. No.: WO2010/103140
PCT Pub. Date: Sep. 16, 2010

(65) Prior Publication Data
US 2012/0076829 A1    Mar. 29, 2012

(30) Foreign Application Priority Data
Mar. 10, 2009  (WO) ................. PCT/ES2010/000097

(51) Int. Cl.
| A61K 35/74 | (2006.01) |
| A61P 37/04 | (2006.01) |
| A61P 3/02 | (2006.01) |
| A61P 1/00 | (2006.01) |
| A61P 3/04 | (2006.01) |
| A61P 3/10 | (2006.01) |
| A61P 31/00 | (2006.01) |
| C12N 1/20 | (2006.01) |

(52) U.S. Cl.
USPC ................. 435/252.9; 435/252.1; 424/282.1; 424/93.4; 424/93.45

(58) Field of Classification Search
None
See application file for complete search history.

*Primary Examiner* — Robert A Zeman
(74) *Attorney, Agent, or Firm* — Sughrue Mion, PLLC

(57) ABSTRACT

The invention relates to probiotic micro-organisms isolated from faeces of children exclusively fed with breast milk. Said microorganisms are used in the food or pharmaceutical industry, especially for use in infant formula milk, due to their probiotic properties which have beneficial effects on the health of those ingesting them. Said microorganisms consist of *Lactobacillus rhamnosus* HERO 22A (CNCM I-4036), *Lactobacillus paracasei* HERO 7 (CNCM I-4034) and *Bifidobacterium breve* HERO 15B (CNCM I-4035).

17 Claims, 13 Drawing Sheets

| Sample | Control | pH 3.0 | % | pH 2.5 | % | pH 2.0 | % |
|---|---|---|---|---|---|---|---|
| LGG | 6.97E+07 | 7.40E+07 | 106.2 | 0 | 0 | 0 | 0 |
| L. casei | 7.53E+07 | 7.30E+07 | 96.9 | 0 | 0 | 0 | 0 |
| 7 | 5.33E+07 | 5.99E+07 | 112.4 | 0 | 0 | 0 | 0 |
| 22A | 7.74E+07 | 7.88E+07 | 101.8 | 6.30E+07 | 81.4 | 5.90E+07 | 76.2 |

FIG 1

| Sample | Control | Oxgall 0.3% | % | Oxgall 0.7% | % |
|---|---|---|---|---|---|
| LGG | 6.97E+07 | 4.03E+07 | 57.8 | 7.13E+07 | 76.1 |
| L. casei | 7.53E+07 | 3.08E+07 | 40.9 | 8.00E+07 | 110.6 |
| 7 | 1.16E+07 | 1.33E+07 | 114.7 | 1.79E+07 | 154.3 |
| 22A | 7.44E+07 | 7.55E+07 | 101.5 | 7.81E+07 | 105.0 |

FIG 2

| Sample | Control | Adhesion | % |
|---|---|---|---|
| LGG | 1.98E+08 | 9.50E+06 | 4.80 |
| L. casei | 3.25E+09 | 1.33E+08 | 4.09 |
| 7 | 1.05E+08 | 7.87E+06 | 7.48 |
| 22A | 5.68E+08 | 6.56E+07 | 11.55 |

FIG 3

| Sample | control | pH 3.0 | % | pH 2.5 | % | pH 2.0 | % |
|---|---|---|---|---|---|---|---|
| B. bifidum | 1.04E+08 | 5.80E+07 | 55.6 | 0 | 0 | 0 | 0 |
| B. longum | 9.62E+07 | 1.01E+08 | 104.8 | 0 | 0 | 0 | 0 |
| 15B | 5.33E+07 | 5.99E+07 | 139.6 | 0 | 0 | 0 | 0 |

FIG 4

| Sample | Control | Oxgal 0.3% | % | Oxgall 0.5% | % | Oxgall 0.7% | % |
|---|---|---|---|---|---|---|---|
| B. bifidum | 7.57E+07 | 7.54E+07 | 99.6 | 6.70E+07 | 88.5 | 7.00E+07 | 92.5 |
| B. longum | 7.51E+07 | 7.54E+07 | 100.4 | 7.20E+07 | 95.9 | 6.90E+07 | 91.9 |
| 15B | 6.10E+07 | 5.30E+07 | 86.9 | 6.00E+07 | 98.4 | 7.50E+07 | 123.0 |

FIG 5

| Sample | Control | Adhesion | % |
|---|---|---|---|
| B. bifidum | 7.80E+06 | 6.90E+05 | 8.8 |
| B. longum | 1.10E+03 | 1.00E+02 | 9.1 |
| 15B | 6.00E+02 | 1.00E+02 | 16.7 |

FIG 6

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| | Control | alkaline phosphatase | esterase (C4) | esterase lipase (C8) | lipase (C14) | Leucine arylamidase | Valine arylamidase | Cysteine arylamidase | Tyrpsine | α-chemotrypsine | Acid phosphatase | Naphthol-AS-B1-phosphohydrolase | α-galactosidase | β-galactosidase | β-glucuronidase | α-glucosidase | β-glucosidase | N-acetyl-β-glucosaminidase | α-mannosidase | α-fucosidase |
| B. bifid | 0 | 2 | 2 | 3 | 1 | 5 | 1 | 4 | 0 | 0 | 3 | 2 | 5 | 5 | 0 | 5 | 1 | 5 | 0 | 0 |
| B. long | 0 | 0 | 2 | 2 | 1 | 2 | 0 | 0 | 0 | 0 | 1 | 1 | 5 | 5 | 0 | 5 | 1 | 2 | 0 | 0 |
| 15B | 0 | 0 | 1 | 1 | 1 | 3 | 0 | 0 | 0 | 0 | 1 | 2 | 5 | 5 | 0 | 5 | 2 | 0 | 0 | 0 |

FIG 7

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| | Control | alkaline phosphatase | esterase (C4) | esterase lipase (C8) | lipase (C14) | Leucine arylamidase | Valine arylamidase | Cysteine arylamidase | Tyrpsine | α-chemotrypsine | Acid phosphatase | Naphthol-AS-B1-phosphohydrolase | α-galactosidase | β-galactosidase | β-glucuronidase | α-glucosidase | β-glucosidase | N-acetyl-β-glucosaminidase | α-mannosidase | α-fucosidase |
| LGG | 0 | 5 | 3 | 4 | 0 | 3 | 5 | 1 | 0 | 0 | 5 | 5 | 2 | 5 | 0 | 2 | 2 | 0 | 0 | 5 |
| L. casei | 0 | 1 | 1 | 5 | 0 | 4 | 5 | 1 | 0 | 0 | 4 | 3 | 0 | 3 | 0 | 5 | 0 | 0 | 0 | 0 |
| 7 | 0 | 3 | 4 | 4 | 0 | 5 | 5 | 1 | 0 | 0 | 4 | 2 | 0 | 4 | 0 | 5 | 0 | 0 | 0 | 0 |
| 22A | 0 | 5 | 5 | 5 | 0 | 4 | 5 | 1 | 0 | 1 | 5 | 5 | 4 | 5 | 1 | 2 | 3 | 0 | 0 | 5 |

FIG 8

| 22A | 7 | L.casei | LGG | |
|---|---|---|---|---|
| - | - | - | - | Control |
| - | - | - | - | Glycerol |
| - | - | - | - | Erythritol |
| - | - | - | ◁ | D-Arabinose |
| - | - | - | - | L-Arabinose |
| + | + | + | ◁ | D-Ribose |
| - | - | - | - | D-Xilose |
| - | - | - | - | L-Xilose |
| - | ◁ | + | - | D-Adonitole |
| - | - | - | - | Methyl-βD-Xylopyranoside |
| + | + | + | + | D-Galactose |
| + | + | + | + | D-Glucose |
| + | + | + | + | D-Fructose |
| + | + | + | + | D-Mannose |
| + | + | + | - | L-Sorbose |
| + | + | - | - | L-Rhammose |
| - | + | ◁ | + | Dulcitol |
| - | - | - | - | Inositol |
| + | + | + | + | D-Mannitol |
| + | + | + | + | D-Sorbitol |
| - | - | - | - | Methyl-αD-Mannopyranoside |
| ◁ | ◁ | ◁ | - | Methyl-αD-Glucopyranoside |
| + | + | + | + | N-Acetylglucosamine |
| + | ◁ | ◁ | + | Amygdalin |
| + | + | + | + | Arbutine |
| + | + | + | + | Aesculin Ferric Citrate |

FIG 9 A

| 22A | J | L. casei | LGG | |
|---|---|---|---|---|
| + | + | + | + | Salicin |
| + | + | + | + | D-Cellobiose |
| ◁ | ◁ | + | - | D-Maltose |
| + | + | + | - | D-Lactose (orbovine) |
| - | - | - | - | D-Meliobiose |
| - | + | ◁ | ◁ | D-Sucrose |
| + | + | + | + | D-Trehalose |
| - | + | - | - | Inulin |
| + | + | - | + | D-Melezitose |
| - | - | - | - | D-Raffinose |
| - | - | - | - | Starch |
| - | - | - | - | Glycogen |
| - | - | - | - | Xylitol |
| ◁ | ◁ | ◁ | + | Gentiobiose |
| + | + | + | - | D-Turanose |
| - | ◁ | ◁ | - | D-Lyxose |
| + | + | + | + | D-Tagatose |
| - | - | - | - | D-Fucose |
| - | - | ◁ | + | L-Fucose |
| - | - | - | - | D-Arabitol |
| - | - | - | - | L-Arabitol |
| ◁ | ◁ | ◁ | ◁ | Potassium gluconate |
| - | - | - | - | 2-potassium ketogluconate |
| - | - | - | - | 5-potassium ketogluconate |

FIG 9 B

ISOLATION, IDENTIFICATION AND CHARACTERIZATION OF STRAINS WITH PROBIOTIC ACTIVITY, FROM FAECES OF INFANTS FED EXCLUSIVELY WITH BREAST MILK

CROSS REFERENCE TO RELATED APPLICATIONS

This application is a National Stage of International Application No. PCT/ES2010/000097 filed on Mar. 9, 2010, which claims priority from Spanish Patent Application No. PCT/ES09/000130, filed on Mar. 10, 2009, the contents of all of which are incorporated herein by reference in their entirety.

TECHNICAL SECTOR OF THE INVENTION

The general objective of this study is to isolate probiotic microorganisms for a subsequent use in the food and pharmaceutical industry, especially for using them in infant formula milk. Said microorganisms have high values of resistance to pH, bile salts and intestinal cell adhesion, they are therefore especially suitable for use in the aforementioned industries.

BACKGROUND OF THE INVENTION

Nutrition has had a very significant development which has changed its concept in the recent decades. Diet was previously considered as having the role of providing nutrients necessary to maintain the health condition, whereas today this concept has evolved into the idea that diet can contain foods which in addition to providing nutrition, promote health. This is the reason why the food industry has started to develop a large amount of products promoting health and wellbeing. In this area the line of functional foods has had a very significant development, where the consumption of probiotics by the population increases daily. The real challenge is to broaden the knowledge of these foods, among them those containing probiotics have a special interest.

There are very old records relating to the beneficial effects derived from the consumption of foods with high bacterial content, such as in the version of the old testament wherein it is said that Abraham attributes his long life to the consumption of milk, or the Roman historian Plinius who in the year 76 B.C. recommended the use of fermented milk products for treating gastroenteritis (Senmier and De Vrese 2001).

At the beginning of the last century, the Russian microbiologist Elie Metchnikoff (1845-1916) suggested that the consumption of fermented milk modulated the intestinal microbiota producing a positive effect in human health (Metchnikoff 1908). He fixed his attention to the fact that there was an incredible number of centenarians in Bulgaria, despite of it being one of the poorest European countries. He observed that the Bulgarians consumed large amounts of yoghurt. Metchnikoff successfully isolated the bacteria responsible for producing the yoghurt and used it in his researches. It was the start of the probiotic study. Metchnikoff became a strong defender of the concept that diet can protect the body from pathogen invasion and therefore improves and prolongs the quality of life. He was also the first person to develop a preparation using *lactobacillus* in the form of capsule to be ingested orally, called Lactobacillin.

At the same time, the French microbiologist Tissier observed that the fecal microbiota of breast-feeding newborns have more bacteria from the genus *Bifidobacterium* than the fecal microbiota of children who have received artificial milk and acknowledged the beneficial role of this microorganism.

Later in 1940, Bifidus Milk appeared to alleviate children nutritional deficiencies during the $1^{st}$ World War. In 1950, the Degusta factory prepares Biogur and Bio-garde. In 1989, the consumption and production of fermented milk increases in Switzerland. In 1993, two researchers, Modler and Vila-García, developed the first low acidity bio yoghurt.

In 1965, Lilly and Stillwell used the term "probiotic" for the first time to name the products of gastric fermentation. But the more valid and widely used definition of probiotic will be that enunciated much later on by Fuller (Fuller 1992, Fuller 1989). Probiotics are defined as: "supplements of live microorganisms which upon being added to foods exert beneficial effects in the health of the receiver as they condition an improvement in his/her intestinal microbial balance". For the adult human being, this includes both products derived from fermented milk and preparations lyophilized with these bacteria.

In 1998, the International Life Science Institute (ILSI) in Brussels defined probiotics as live microorganisms, which when ingested in sufficient amounts, have beneficial effects on health, which effect is way above the conventional nutritional effects. They beneficially affect one or several functions of the organism. They provide a better health condition and wellbeing and/or reduce the risk of disease. They can be functional for the general population or for particular groups thereof.

Today there are criteria for the definition of probiotic microorganisms:
1. They are of human origin.
2. They are of non-pathogenic nature.
3. They are resistant to destruction by technical processes.
4. They are resistant to destruction by gastric acid and bile.
5. They adhere to the intestinal epithelium.
6. They are capable of colonizing the gastrointestinal tract.
7. They produce antimicrobial substances.
8. They modulate the immune response.
9. They influence the human metabolic activities (cholesterol assimilation, vitamin production, etc).

The probiotic bacteria can influence all the intestinal cells and the mechanisms of action of these cells including the effects on the microbiota (Backhed and Ley 2005), the modulation of the immune function (Picard et al. 2004; Kalliomaki 2004) and the increase of the epithelial barrier function (Madsen et al. 2001; Isolauri & Salminen 2005).

Among the bacteria with probiotic activity, those from the genus *Bifidobacterium* are the most abundant in the intestine with 25% of bacteria in the adult colon and 95% in the breast-feeding newborn. There are many food products (yoghurt and milk) today which are supplemented with this type of bacteria. Other strains which also have probiotic activity are those from the genus *Lactobacillus*, which according to "in vitro" studies inhibit the adhesion of other anaerobic bacteria such as *clostridium, bacteroides, bifidobacterium, pseudomonas, staphylococcus, streptococcus* and enterobacteriaceas (Silva et al. 1987).

The use of probiotics as medical tool in some pathologies is very well-received and the proof of the effectiveness thereof is strong, mainly as the result of the clinical studies and meta-analysis, for malabsoprtion of lactose, (Adolfsson et al. 2004; Piaia et al. 2003) gastrointestinal infections (Brownlee et al. 2003) and diarrhea associated to the use of antibiotics (D'Souza et al. 2002). Furthermore, the use of probiotic bacteria either bifidobacteria, lactobacillus and/or a mixture thereof have shown beneficial effects on some digestive diseases. There is much proof in the literature on the beneficial effects.

The understanding of the relationship existing between the components of the intestinal microbiota as well as the interaction with the host is very complex. The genome facilitates analyzing the isolated bacteria response to the intestinal conditions, partly revealing the metabolic capacity of the strains, however, the conditions in which these capacities can be expressed, as well as the conditions to enable isolating most of the strains forming the intestinal microbiota is still largely unknown, it being able to be identified only by means of molecular tools identifying their genome partly or completely. Due to this reason the development in the area of the probiotics and functional foods is in full development.

Thus, taking into account that there are different effects between the probiotic strains and that varieties of bacteria belonging to the same species may present different physiological characteristics rendering them different or improved probiotic properties against other bacteria, the identification and characterization of the effects of new prebiotic strains is very important in view of their health and industrial interest.

The general objective of this study is to isolate probiotic microorganisms with improve probiotic properties resistance to an acidic pH, resistance to bile salts and intestinal cell adhesion for a subsequent use in the food and pharmaceutical industry especially for using them in infant formula milk.

The present invention provides and characterizes probiotic microorganisms isolated from faeces of children fed exclusively with breast milk.

The greater resistance of the strains object of the invention to pH and bile salts confers the probiotic microorganisms a greater survivability as they pass through the stomach and intestine and thus increases their colonizing effect and therefore their antagonic effects against other potentially pathogenic bacteria. On the other hand, the greater adherence of the probiotics strains making up the object of the invention to the human intestinal cells enables a greater action on all immune system modulation.

OBJECT OF THE INVENTION

The present invention provides probiotic microorganisms isolated from faeces of children fed exclusively with breast milk. Said microorganisms, are used in the food or pharmaceutical industry, especially for use in infant formula milk, due to their probiotic properties which have beneficial effects on the health of those ingesting them.

For the isolation of said probiotic microorganisms, the present invention proposes the following specific objectives: a) isolating lactic acid bacteria stains obtained from faeces of exclusively breast-fed children; b) evaluating the resistance to pH and bile salts; and c) evaluating the adherence to intestinal epithelial cells.

It is common to look for probiotic bacteria in the faeces of babies. Furthermore, there is certain tradition recommending that the probiotics must be of human origin, supposedly because they would be better implanted in human intestine. However, many of the isolated strains do not meet the probiotic condition since they are rarely or are not resistant to the digestive juices and many of them do not adhere to the intestinal epithelium. In the present invention babies fed exclusively with breast milk are selected to assure that the bacteria isolated is not commercial bacteria. Furthermore, it has been shown that the intestinal microbiota of babies fed with breast milk is very rich in bifidobacteria and *lactobacillus*.

Relating to the probiotics, an effective probiotic must be characterized by:
1. Its capacity to exert a beneficial effect on the host eg. resistance to diseases.
2. It does not cause pathogenicity or toxicity.
3. Its capacity to survive upon passing through the intestinal tract. Eg. resistance to gastric acid and bile acids.
4. Its capacity to maintain the adherence to the cells of the intestinal wall.
5. Its short, stable generation time and its ability of being viable for long periods under storage conditions.
6. It is of human origin.
7. It produces antimicrobial substances against pathogens, antineoplastic properties.
8. Its ability of influencing the metabolic activity.

Among the health advantages associated to probiotic ingestion are:
1. Relief of symptoms derived from the malabsorption of lactose.
2. Increment of the natural resistance to infectious diseases of the intestinal tract.
3. Reduction of the serum cholesterol concentration.
4. Digestion improvement.
5. Stimulation of gastrointestinal immunity.
6. Development of immunotolerance to food antigens and reduction of the risk of allergies Thus, the present invention relates to new probiotic microorganisms isolated from faeces of babies. The invention specifically relates to the *Lactobacillus rhamnosus* HERO 22A (CNCM 1-4036), *Lactobacillus paracasei* HERO 7 (CNCM 1-4034) and *Bifidobacterium breve* HERO 15B (CNCM I-4035) microorganisms. Said microorganisms have improved probiotic properties against microorganisms of the same species.

Formulation relates to the compositions or group of one or several ingredients, i.e., class and number of the elements present in a complex substance (food product or dosage form, among others) and proportion in which they are found.

"Carrier" is understood as any type of substance allowing the growth, transportation and/or administration of the strains of the present invention. Depending on the purpose and/or use to which said strains are intended for, the "carriers" could be of different nature. The present invention relates to pharmaceutically acceptable "carriers" such as those commonly associated to capsules, tablets or powder, as well as a "carriers" formed by ingredients or food products.

The food products intended for special diets are food products which due to their particular composition or the particular process for manufacturing them, are clearly distinguished from the staple food products, which are suitable for the nutritive objective indicated and which are marketed indicating that they fulfill said objective. (Council Directive 89/398/EEC of 3 May 1989 related to the approximation of the laws of the Member States on the food products intended for special diets (DO series L no. 186 of 30 June)).

Special diets is understood as that which must fulfill the particular nutritional needs of:
i) determined classes of people who have assimilation process or metabolism disorder, or
ii) determined classes of people who are in particular physiological conditions and who, therefore, obtain special benefits from a controlled ingestion of determined food substances, or
iii) babies or young children with good health.

Food supplement relates to those food products the purpose of which is to complement the normal diet and consisting of concentrated sources or nutrients or other substances which have a nutritional or physiological effect in a single or combined manner, marketed in dosage form, i.e. capsules, pills, tablets, pastilles and other similar forms, powder sachets, liquid ampoule, bottles with droppers and other similar forms of liquids and powders which must be taken in small unitary amounts; (Directive 2002/46/EC of the European Parliament and Council of 10 Jun. 2002 related to the approximation of the laws of the Member States in food supplement matter).

Probiotic relates to those microbial cell preparations or microbial cells or components of microbial cells with a beneficial effect on the health and the wellbeing of the host.

Prebiotic is understood as "a non-digestible ingredient from the diet which benefits and stimulates the intestinal bacteria growth improving the intestinal balance of the host". Among the prebiotics used are: inulin, oligofructosaccharides, galactooligosaccharides, oligosaccharides coming from the hydrolysis of pectins and other rubbers and mucilages, and resistant starches and maltodextrins as well as nucleotides.

An object of the present invention relates to the strain of probiotic microorganism isolated from faeces of children fed exclusively with breast milk characterized by consisting *Lactobacillus rhamnosus* HERO 22A (CNCM 1-4036) or *Lactobacillus paracasei* HERO 7 (CNCM 1-4034) or *Bifidobacterium breve* HERO 15B (CNCM I-4035).

In a particular embodiment, said strain is *Lactobacillus rhamnosus* HERO 22A (CNCM I-4036).

In another particular embodiment, said strain is *Lactobacillus paracasei* HERO 7 (CNCM 1-4034).

In another particular embodiment, said strain is *Bifidobacterium breve* HERO 15B (CNCM I-4035).

In an embodiment, the strain previously described is presented in the form of pure biological culture. In another embodiment the strain is isolated.

In an embodiment the strain of microorganism previously described is presented in the form of viable cells; in another embodiment the strain is presented in the form of non-viable cells.

Another object of invention relates to the formulation comprising a strain of microorganism as has been previously described. In a particular embodiment, said formulation comprises another probiotic material, in another embodiment, it additionally comprises prebiotic material.

In another particular embodiment the formulation described comprises a carrier suitable for ingestion. Said carrier is pharmaceutically acceptable such as those commonly associated to capsules, tablets or powder.

In another particular embodiment said carrier is a food product. Said food product is selected from the group consisting of milk and milk-derived products, especially fermented milk and cheeses; cereals and derivatives including bread doughs; soups and other similar products in dehydrated form; fermented meat products; fruit derivatives, juices and soft drinks; foods for specific nutritional uses.

Another object of invention relates to the strain of probiotic microorganism or the formulation previously described for use in diets. In an embodiment, said diets relate to infant and/or adult and/or special diets.

In another embodiment, the strain of probiotic microorganism or the formulation previously described are used for the preparation of infant formula milk. In a particular embodiment, said formulas consist of ready-to-eat infant milk and/or infant cereals, and/or infant foods.

In another embodiment, the strain of probiotic microorganism or the formulation previously described are used for the preparation of food supplements.

In another embodiment, the strain of probiotic microorganism or the formulation previously described are used for the preparation of special formulas for oral and/or enteral nutrition.

In another embodiment the strain of probiotic microorganism or the formulation previously described are used for the preparation for pharmaceutical application/applicable as medicinal product/for use in the preparation of a pharmaceutical product.

In another embodiment, the strain of probiotic microorganism or the formulation previously described are applicable in stimulating the immune system and/or in preventing/treating asthma and/or in preventing/treating gastrointestinal disorders, and/or in eliminating/modulating the main digestive pathogens, and/or in preventing/treating obesity and its co-morbidities included the metabolic syndrome and diabetes and/or in the aging-associated diseases.

Said gastrointestinal disorders comprise alterations of intestinal transit such as constipation and alterations of the bioavailability of minerals, infections and malabsorption syndromes.

Said malabsorption syndromes comprise disorders affecting the anatomy of the intestine such as short bowel syndrome and disorders affecting the physiology of the intestine such as cystic fibrosis of the pancreas, malabsoprtion of sugar especially lactose, alterations of the lipid absorption, food allergies, and inflammatory bowel diseases such as Crohn's disease and ulcerative colitis.

DESCRIPTION OF THE DRAWINGS

FIG. 1 shows, through a table, the influence of pH on the survival of the *Lactobacillus rhamnosus* CNCM I-4036 and *Lactobacillus paracasei* CNCM I-4034 strains, object of the invention, compared with two commercialized strains. Specifically, said table shows the values of viability (in % of colony forming units from the pH resistance studies of the isolated *Lactobacillus rhamnosus* 22A (CNCM I-4036), *Lactobacillus paracasei* 7 (CNCM I-4034) strains and their respective commercial controls. Said values are shown as % of survival by comparing the number of bacteria present in the control to the number of bacteria present at the different pH tested. The results are expressed in units of percentage in the % column. It can be observed that at pH 3 the strains 7 and 22A have a similar or slightly higher resistance than the tested commercial strains. Nevertheless, at pH 2 the strain 22A has a very high viability compared with the rest of the strains which do not survive at this pH.

FIG. 2 shows, through a table, the influence of the bile salts (Oxgall) on the survival of the *Lactobacillus rhamnosus* CNCM I-4036 and *Lactobacillus paracasei* CNCM 1-4034 strains, object of the invention, compared with two commercialized strains. Thus, said table shows the values of viability from the bile salt resistance studies of the isolated strains *Lactobacillus rhamnosus* 22A (CNCM 1-4036), *Lactobacillus paracasei* 7 (CNCM 1-4034) and their respective commercial controls. Said values are shown as % of survival in comparison with the number of bacteria present in the control to the number of bacteria present at the different concentrations of bile salts tested. The results are expressed in units of percentage in the % column. As inferred from the results, both strains 7 and 22A show a much higher percentage of survival, about two times higher, than the tested commercial strains both at the concentrations of 0.3% and 0.7% of bile salts. Both strains have a survival rate greater than 100% indicating that they can even reproduce in the presence of these salts. This indicates, together with their high resistance to pH, a high colonizing potential of the strains.

FIG. 3 shows, through a table, the adhesion to human intestinal HT-29 cells of the *Lactobacillus rhamnosus* CNCM I-4036 and *Lactobacillus paracasei* CNCM I-4034 strains, object of the invention, compared with two commercialized strains. Said capacity is shown through the values of viability from the intestinal epithelial cell adhesion studies of the isolated *Lactobacillus rhamnosus* 22A (CNCM 1-4036), *Lactobacillus paracasei* 7 (CNCM 1-4034) strains and their respective commercial controls. Said values are shown as % of bacteria adhered in comparison with the number of bacteria present in the control. Both strains present percentages of adhesion to the human intestinal HT-29 cells much higher than that of the tested commercial strains, which indicates their potential action in modulating the intestinal cell activities included immunomodulation.

FIG. 4 shows, through a table, the influence of pH on the survival of the strain *Bifidobacterium breve* CNCM 1-4035, object of the invention, compared with two commercialized strains. Said influence is shown through the values of viability from the pH resistance studies of said strain in comparison to its respective commercial controls. Said values are shown as % of survival by comparing the number of bacteria present in the control to the number of bacteria present at the different tested pH. The results are expressed in units of percentage in the % column. It can be observed that at pH 3 the strain 15B shows a resistance significantly much greater than that of the other two bifidobacteria tested, its viability being 100% greater than 100% indicating that the bacteria can even reproduce at that pH.

FIG. 5 shows, through a table, the influence of the bile salts (Oxgall) on the survival of the strain *Bifidobacterium breve* CNCM I-4035, object of the invention, compared with two commercialized strains. This influence is shown by means of bile salt resistance studies of the isolated strain *Bifidobacterium breve* 15B (CNCM I-4035) and its respective commercial controls. Said values are shown as % of survival by comparing the number of bacteria present in the control to the number of bacteria present at the different concentrations of bile salts tested. The results are expressed in units of percentage in the % column. The values of survival in the presence of bile salts at low concentrations are similar to those of the other two bifidobacteria. However, the strain 15B shows a greater survival at higher concentrations.

FIG. 6 show, through a table, the adhesion to human intestinal cells of the *Bifidobacterium breve* CNCM I-4035 strain, object of the invention, compared with two commercialized strains. Said capacity is shown through the values of viability from the intestinal epithelial cell adhesion studies of the isolated strain *Bifidobacterium breve* 15B (CNCM I-4035) and its respective commercial controls. Said values are shown as % of bacteria adhered in comparison with the number of bacteria present in the control. The strain object of the invention has a percentage of adhesion to the human intestinal HT-29 cells much higher than that of the commercial strains tested, which indicates its potential action in modulating of intestinal cell activities including immunomodulation.

FIG. 7 shows the enzymatic activities (in units of: Units/ml of culture medium) of the strain *Bifidobacterium breve* CNCM I-4035 (*Bifidobacterium breve* 15B), object of the invention, compared with two commercialized strains (its controls). The results are expressed as described in Example 11. The results obtained allow concluding that the fermentative activity of CNCM I-4035 coincides with that of a species from the genus *Bifidobacterium*, allowing classifying CNCM I-4035 inside said genus FIG. 8 shows the enzymatic activities of the Lactobacillus rhamnosus CNCM 1-4036 (*Lactobacillus rhamnosus* HERO 22A) and Lactobacillus paracasei CNCM 1-4034 (*Lactobacillus paracasei* HERO 7) strains, object of the invention, compared with two commercialized strains (controls). The results are expressed as described in Example 11. The results obtained allow concluding that the fermentative activity of HERO 7 and HERO 22A coincides with that of a species from the genus *Lactobacillus paracasei* and *Lactobacillus rhamnosus*, allowing to classify CNCM I-4036 and CNCM I-4034 inside said respective genus and species.

FIG. 9-FIGS. 9A and 9B show the results of the fermentative activities of carbohydrates and other substrates (API 50 CHL) of the selected CNCM I-4034 (*Lactobacillus paracasei* HERO 7) and CNCM I-4036 (*Lactobacillus rhamnosus* HERO 22A) strains and their controls. The results are expressed as described in Example 11. The results obtained allow concluding that the fermentative activity of HERO 7 (CNCM I-4034) and HERO 22A (CNCM I-4036) coincide with that of the species from the genus *Lactobacillus paracasei* and *Lactobacillus rhamnosus*, allowing classifying CNCM I-4036 and CNCM I-4034 inside said genus.

FIG. 10-FIGS. 10A, 10B and 10C show the results of the effect exerted by the probiotic bacteria of the present invention on *L. monocytogenes* CECT 4031 and *S. sonnei* CECT 457. (A) effect exerted on *L. monocytogenes* CECT 4031 from supernatant concentrated 10× obtained after 17h of *L. paracasei* CNCM I-4034 growth. (B) effect exerted on L. monocytogenes CECT 4031 from supernatant concentrated 10× obtained after 24h of *B. breve* CNCM I-4035 growth. (C) effect exerted on *S. sonnei* CECT 457 from supernatant concentrated 10× obtained after 24 hours of *L. rhamnosus* CNCM 1-4036 growth.

DETAILED DESCRIPTION OF THE INVENTION

Figure 10A:
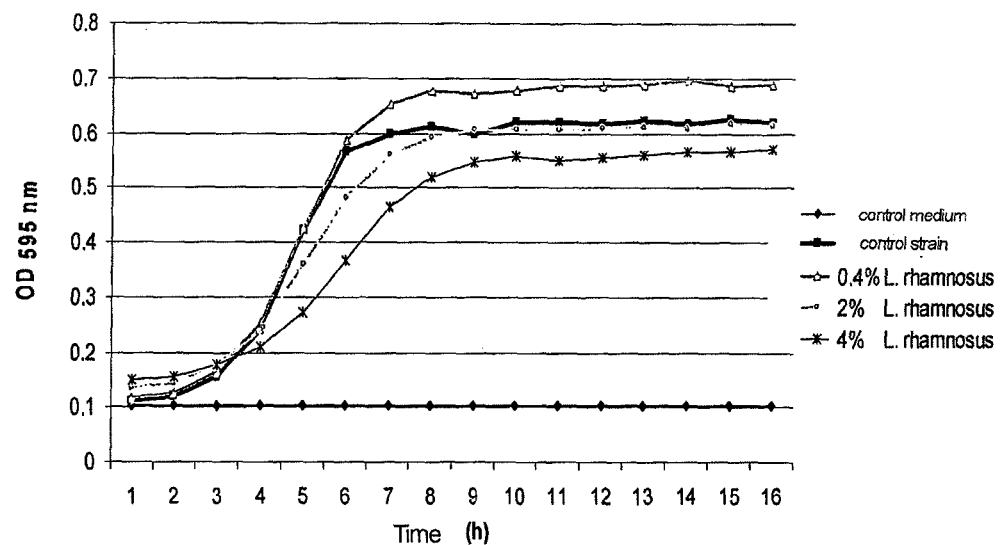

The present invention provides probiotic microorganisms with improved probiotic properties of resistance to pH, bile salt and adhesion. Specifically, the present invention isolates and characterizes the bacteria *Lactobacillus rhamnosus* HERO 22A (CNCM I-4036), *Lactobacillus paracasei* HERO 7 (CNCM I-4034) and *Bifidobacterium breve* HERO 15B (CNCM I-4035), isolated from faeces of babies.

It is known that the mucosal surfaces are colonized by a large amount and a great diversity of microorganisms. In adults, there are numerically more prokaryotic cells than eukaryotic cells, in fact it is estimated that 90% of human cells are microbial cells, whereas only 10% correspond to eukaryotic cells (Savage 1977). The influence of this microbial community on human physiology is probably more obvious in the intestine due to the fact that this organ contains most of these organisms. The density in the proximal and mid-small intestine is relatively low, but there is a considerable increase in the distal small intestine which can reach $10^8$ cfu/ml of luminal content and in the colon up to $10^{11}$-$10^{12}$/g.

During the first few days of life, there is a great change in the composition of the intestinal microbiota. In birth, the intestine is sterile and within the first few hours of life the bacteria start to appear in the stools. The gastrointestinal tract is first colonized by the maternal vaginal and fecal bacterial flora. The first microorganisms colonizing the intestine are those which have a high reducing power, including species such as *enterobacteria, streptococcus* and *staphylococcus*. The consumption of oxygen by these bacteria gradually changes the intestinal environment, allowing the growth of anaerobic bacteria including *lactobacillus* and bifidobacteria. These bacteria colonizing the newborn are mainly from the mother and the environment, the type of delivery being one of the main determinants of the intestinal microbiota (Bezirtzoglou 1997).

The intestinal ecosystem is formed by the interaction between the microbiota, the intestinal epithelium, mucosal immune system, and enteric nervous system (Gordon et al. 1997). The comparison of normal rats and rats with germ-free intestine has revealed a series of anatomic, biochemical and physiological differences. For example, the presence of the microbiota increase the epithelial exchange, it also conjugates and removes the hydroxyl group from the bile acids, metabolizes the bilirubin and reduces the cholesterol to coprostanol.

Therefore, the relationship between intestine and microbiota is very close and it can be seen as a symbiosis relationship because, for example, the microbiota can degrade carbohydrates that cannot be degraded by the intestine due to lack of enzymatic machinery. The products generated by this degradation are mainly used as nutrients for the intestinal epithelium as occurs with the short chain fatty acids. Furthermore, the presence of this microbiota has an immunomodulation effect since the main physiological characteristic of the intestinal mucosa is the capacity of starting an energy response against invasive pathogens which can colonize the intestinal epithelium, and at the same time having a zero response to bacteria contained in foods or against the resident microbiota. This lack of response is an active process of several mechanisms known as oral tolerance. This process is essential so that the host does not develop an inflammatory response to the presence of any microorganism and thus can have different responses to different microorganisms, thus aiding the stability of the intestinal flora. This is the reason why having a microbiota of normal composition can aid the host in physiological, immune and metabolic development. This ecosystem is maintained in equilibrium and any cause disrupting this equilibrium can trigger a pathology (diarrheas, inflammatory diseases).

It is of interest to understand the importance of this ecosystem, the function of non-pathological strains or "good bacteria". The concept of probiotics as human health mediators has been developed on this idea. Within the different areas studied, the influence of the probiotics on the modulation of the gene expression in different situations is one of the most interesting.

As indicated previously, the present invention isolates lactic acid bacteria and bifidobacteria with improved probiotic properties from faeces of exclusively breast-fed children. To that end, the pH resistance, bile salt resistance and the intestinal epithelial cell adhesion capacity of the isolated bacteria were assessed. The fundamental results of the present invention indicate that in the faeces of these babies there are bacteria which are highly resistant to gastric pH, to bile salts and with intestinal epithelial cell adhesion capacity, which can be used as probiotics.

To check the probiotic activity of the bacteria, they must first be subjected to a series of in vitro assays simulating the conditions at which said bacteria will be subjected to in the organism, they must remain viable in said conditions and therefore preserve their beneficial health properties. In the present invention, the control bacteria used (Example 12) which in comparison to the bacteria of the invention show their improved probiotic properties are, for Bifidobacteria: *Bifidobacterium bifidum* and *Bifidobacterium longum* supplied by Hero España S. A., and for *Lactobacillus*, 2 commercial lactobacillus are used: *Lactobacillus casei* (Danone®) and *Lactobacillus rhamnosus* GG (LGG) (VALIO®).

By taking into account the interest of the bacteria making up this invention in the stimulation of the immune system and in its action on the main digestive pathogens, these control bacteria have been selected because they are marketed today on an international level in the form of fermented milk and in other dosage forms and there are several publications on their probiotic effects especially in preventing acute diarrhea in children and modulating the immune system in both animals and humans Thus, the in vitro assays indicated relate to:

Resistance to Gastric Acidity

Before reaching the intestinal tract, the probiotic bacteria must survive their passage through the stomach (Henriksson et al. 1999). The gastric acid secretion in the stomach forms a first defense mechanism against most of the microorganism load entering through the oral route. Therefore, the survival of the bacterial strains in gastric acid is the most accurate indication of their ability to pass through the stomach. The University College of Cork-based Probiotic Research Group successfully isolated and identified lactic acid bacteria which showed ideal probiotic features (Dunne et al. 1999). Preliminary experiments were carried out to determine the degree of initial resistance which the *lactobacillus and* bifidobacteria strains isolated from the human ileum have. The human gastric juice was obtained from healthy individuals by aspiration through a nasogastric tube. Since the pH in the stomach fluctuates (it can reach 1.5), it was measured before use. This acid was added to the RSM medium (Rogosa Sharpe Medium). The initial survival of the strains was evaluated as 108% and 106% for *Lactobacillus* and *Bifidobacterium*, respectively, in RSM medium (De Man et al 1960) with HCl changing the pH value between 2.0 and 3.4. The results showed a great *Bifidobacterium* sensitivity to the acidity (Thornton 1996). Thus, the strains making up the present invention have resistance values greater than those of the strains studied in said experiments, i.e. they have greater resistance to acidity (FIGS. 1 and 4).

Resistance to Bile Salts

As has been explained above, to characterize a probiotic potential, this must also be capable of resisting bile salts (Lee and Salminen 1995). Bile acids are synthesized in the liver from cholesterol and are secreted from the gall bladder to the duodenum in the form of conjugates (500-700 mL/day) these acids experience more chemical modifications (deconjugation, dehydrolyzation, dehydrogenation, and deglucuronidation) in the colon almost only as a result of the microbial activity. Both conjugated and deconjugated acids have antibacterial activity inhibiting the growth of *Escherichia coli*, *Klebsiella* sp., and *Enterococcus* sp strains in vitro (Lewis et al 1972; Stewart et al 1986). The deconjugated forms are more inhibitory and the gram positive are more sensitive than the gram negative (Floch et al. 1972; Percy-Robb 1972). The Dunne group (Dunne et al. 1999) has chosen, in a first assay, to use a solid growth medium supplemented with bovine, porcine and human bile acid up to a final concentration of 0.3% and 7.5% to assess the bile salt resistance of the strains. After allowing the *lactobacillus* and bifidobacteria to grow, the result was that they showed resistance to the bovine bile acid and that the result of porcine bile acid was much more inhibitory for both bacterial groups (Thornton 1996). Thus, relating to the search for the possible probiotic for human consumption, the most relevant result is the capacity thereof to grow in human bile. By taking into account that human bile is not standardized and that their bile acid content greatly varies from one individual to another, the use of bovine bile standardized in its bile acid content (OXGALL) as the substitute of the human biles is a common practice in the state of the art, allowing protocolizing reproducible assays. This has been the method followed in the present invention for studying the bile salt resistance of the bacteria making up the present invention. The results obtained show that said bacteria have greater resistance to bile salt than their commercial controls (FIGS. 2 and 5).

Intestinal Epithelium Adherence of Probiotic Strains

The adhesion of the strains adhered to the intestinal epithelia tissue and the ability to colonize the gastrointestinal tract must also be evaluated in the selection. The importance of this action resides in the fact that after being selected, many of the probiotics are not further capable of colonizing their target host. In fact, of the probiotics available today, it seems that only *L rhamnosus* GG remains inside the gastrointestinal tract for a significant time period (Berg et al. 1998; Goldin et al. 1992 *L. rhamnosus* GG adheres to Caco-2 cells, HT-29 cells and Caco-2 cells belonging to human intestinal cell lines, they express the morphological and physiological characteristics of a normal human colonocyte and are used to test the mechanisms mediating the enteropathogen adhesion (Bernet 1994). In recent studies they have been used for the selection performed, and thus evaluating the possible lactic acid bacteria or bifidobacteria based on their adhesion capacity (Coconnier et al 1992; Bernet et al. 1993; Greene & Klaenhammer 1994; Crociani et al 1995; Sarem et al. 1996; Tuomola & Salminen 1998).

From the studies performed with these cell lines it is inferred that the adherence of the lactobacillus strains of the present invention which is of the order of 9% on Caco-2 cells and of the order of 5% on HT-29 cells (Tuomola et al, 1998; Dunne et al, 2001; Botes et al, 2008) is very high (7.5% for *L. rhamnosus* CNCM I4036 and 15.5% for *L. paracasei* CNCM I-4034 (FIG. 3) in comparison with the well characterized *Lactobacillus rhamnosus* GG strain. The state of the art contemplates that the adhesion of the bifidobacteria is small in comparison with the lactobacillus, regardless of their species (Dunne et al, 2001). However, the *Bifidobacterium bifidum* and *B. longum* strains used by the company HERO España, which have been considered as controls in the present invention, adhere to HT-29 cells with values close to 9%. Likewise, the bifidobacteria object of the present invention adhere to said cells with a much greater value of 16.7% (FIG. 6).

Selection of the Bacteria

Thus, in the present invention, the bacteria was selected using specific culture media (Example 4) both for bifidobacteria and for *lactobacillus*. During the isolation three new culture media described as being specific for bifidobacteria were used, these are: BFM medium (Nebra and Blanch 1999), Modified Columbia medium and Beerens medium (Beerens 1991. Examples 4.1, 4.2 and 4.3), whereby better result in obtaining bifidobacteria colonies was obtained. To select *lactobacillus*, the culture medium used was Rogosa agar medium (Example 4.4).

In the present invention, the bacteria colonies from the different children which were incubated and subjected to the selection tests were 4680 colonies. After the first assay of resistance to pH 3.0 and to bile salts, there were 758 colonies with a viability of 90%, after the tests of adhesion to the intestinal epithelial cells there are only 90 colonies (Examples 5, 6 and 7)

These colonies were separated into lactobacillus and bifidobacteria according to the culture medium of origin. Their molecular identification (Example 10) by means of amplifying the 16S rRNA gene of each colony for the subsequent sequencing and homology search thereof in the NCBI (BLAST) database was directly performed.

Finally, there were 29 bacterial strains isolated from the Beerens medium, 13 from the Rogosa medium and 10 from the modified Columbia medium, which successfully passed the selection. Given the number of the selected colonies, as has been explained, their molecular identification by means of amplifying the 16S rRNA gene of each colony for the subsequent sequencing and homology search in the NCBI (BLAST) database was directly performed.

The strains classified as lactobacillus were sequenced and these sequences were aligned with each other to know whether bacteria with the same 16s rDNA gene existed, and 41 bacteria which can be separated into 2 groups were found:

A group which had a homology of 99% of a 1474 by fragment of the 16s rDNA gene with:
Lactobacillus rhamnosus strain R-11
Lactobacillus rhamnosus strain La
Lactobacillus rhamnosus, strain: MNFLM01
Lactobacillus rhamnosus strain IDCC 3201
Lactobacillus rhamnosus strain: YIT 0105 (=ATCC 7469)
Lactobacillus rhamnosus strain Lcr35 16S With these results, a bacteria with the best values from the resistance tests was selected from the group (Examples 7 and 9) and was called *Lactobacillus rhamnosus* HERO 22A, (subsequently numbered by the Pasteur Institute [CNCM National Collection of Microorganism Culture PASTEUR INSTITUTE 25, Rué du Docteur Roux F-75724 Paris] as *Lactobacillus rhamnosus* CNCM 1-4036 where it was deposited on 2 Jul. 2008).

The other group which had a homology of 100% of a 1276 by fragment of the 16s rDNA gene with:
Lactobacillus paracasei, strain: T11-9
Lactobacillus paracasei, strain: T7-10
Lactobacillus casei strain KLDS 1.0720
Lactobacillus casei strain L5
Lactobacillus casei, strain: YIT 0209 (=NCDO 151)
Lactobacillus casei, strain: YIT 0180 (=ATCC 334)
Lactobacillus paracasei strain IMPC 2.1
Lactobacillus paracasei, strain: NRIC 1944
Lactobacillus paracasei, strain: NRIC 1942
Lactobacillus paracasei, strain: NRIC 1938
Lactobacillus paracasei, strain: NRIC 1934
Lactobacillus paracasei, strain: NRIC 0638
Lactobacillus casei ATCC 334
Lactobacillus paracasei strain DJ1
Lactobacillus casei strain Ru2-2i
Lactobacillus paracasei isolate 3C
Lactobacillus paracasei isolate 2C
Lactobacillus paracasei
Lactobacillus casei strain MCRF-284
Lactobacillus sp. L02
Lactobacillus paracasei
Lactobacillus paracasei, strain SM20
Lactobacillus casei strain BL23
Lactobacillus paracasei subsp. Paracasei
Lactobacillus paracasei subsp. Paracasei
Lactobacillus casei
Lactobacillus paracasei subsp. Tolerans With these results, a bacteria with the best values of the resistance tests (Examples 7 and 9) was selected from this second group and was initially called *Lactobacillus paracasei* HERO 7, (subsequently numbered by the Pasteur Institute [CNCM National Collection of Microorganism Culture PASTEUR INSTITUTE 25, Rué du Docteur Roux F-75724 Paris] as *Lactobacillus paracasei* CNCM 1-4034 where it was deposited on 2 Jul. 2008).

Subsequently, the same was performed with the group of the bifidobacteria, only a single group which had a homology of 100% of a 1136 by fragment of the 16s rDNA gene with the following being found:
Uncultured bacterium clone rRNA235
Bifidobacterium breve, strain: ATCC 15700

With these results, a bacteria of the group of bifidobacteria with the best results of resistance (139.6% at pH 2.5) (Examples 7 and 9) was selected and was initially called *Bifidobacterium breve* HERO 15B, (subsequently renamed by the Pasteur Institute [CNCM National Collection of Microorganism Culture PASTEUR INSTITUTE 25, Rué du Docteur Roux F-75724 Paris] as *Bifidobacterium breve* CNCM I-4035 where it was deposited the 2 Jul. 2008).

Thus, these bacteria classified as:
Lactobacillus rhamnosus HERO 22A
Lactobacillus paracasei HERO 7
Bifidobacterium breve HERO 15B.
and were sent to the Pasteur Institute for their deposit where they were recognized as unique and were assigned the following final denomination:

| Initial Denomination: | Final Denomination: |
|---|---|
| Lactobacillus paracasei HERO 7 | CNCM I-4034 |
| Bifidobacterium breve HERO 15B | CNCM I-4035 |
| Lactobacillus rhamnosus HERO 22A | CNCM I-4036 |

Results of Resistance to pH, Bile Salts and Cell Adhesion

As indicated above, in order for the probiotic strains to exert a beneficial effect on the intestine, they must survive passage through the stomach, resisting its acidity (pH 2.5-3.5) (Holzapfel et al. 1998) and on the other hand, they must be resistant to bile salts present in the small intestine in order to reach the colon (Otles et al. 2003).

In the present study, the bacteria were incubated at pH 3.0 for 3 hours, although it has been described that 90 minutes should be enough to reproduce the time elapsing between the entrance to and exit from the stomach (Jin et al. 1998). In this case, the isolated strains and the controls presented a viability close to 100% (Example 12/FIGS. 1 and 4) but the exposure to pH 2.5 showed it was very selective because no control presented viability and only the *Lactobacillus rhamnosus* 22A (CNCM I-4036) strain did. In other words, the strain of the invention *Lactobacillus rhamnosus* 22A is considerably more resistant to acid than the control bacteria therefore its passage into the gastrointestinal tract and subsequent colonization are aided. On the other hand, the strain *L. rhamnosus* 7A of the invention presents greater viability at pH 3.0 than the strains used as controls (Example 12, FIGS. 1, 4), which means greater passage into the small intestine.

The viability of probiotic cultures at pH 3.0 for 2 hours and in media containing 500-1000 mg (0.05-0.1%) of bile acids per liter, are considered standard tests of tolerance to acid and bile salts (Snelling 2005), although concentrations of 0.3% of bile salts would be suitable for selecting probiotics. The bile salt tests conducted at different concentrations (0.3% and 0.7%) presented values greater than 100% in all cases for the bacteria object of the invention and greater than the commercial bacteria used as controls (Example 12, FIGS. 2 and 5). In conclusion, the *lactobacillus* strains of the invention are more resistant to pH and bile salts than other bacteria used as probiotics today.

It has been described that the lactobacillus in general present a greater resistance to the gastrointestinal conditions, especially with respect to acidity and bile salts (Ross et al. 2005). The results found are consistent with this description since the values of resistance to the gastrointestinal conditions are slightly higher in *lactobacillus* than in bifidobacteria.

As also mentioned above, another very important aspect for the entrance of probiotics into intestinal microbiota is the adhesion capacity on intestinal epithelial cells, since they prevent the probiotic strains from being eliminated due to peristaltic movements and other bacteria forming the intestinal microbiota. Furthermore, adhesion is the first step in colonization and it is probably a prerequisite for the competitive exclusion of enteropathogens (Forestier et al. 2001; Lee et al. 2003) and for the immunomodulation of the host (Ouwehand et al. 1999; Plant and Conway 2002).

In the present invention, the properties of adhesion of the different strains were studied using HT-29 cells as an in vitro model of intestinal epithelium (Example 12, FIGS. 3 and 6). The adhesion pattern showed to be specific for each strain since they presented very different values even though they are from the same species. This can be understood by comparing the adhesion capacity of different probiotics described, for example, *Lactobacillus casei* (Fyos®) presents adhesion of 14.4%, whereas Lactobacillus casei (*Lactophilus*®) presents adhesion of 2.6% (Morata De Ambrosini et al., 1999). As indicated above, the adherence of the *lactobacillus* strains of the present invention is much greater (7.5% for *L. rhamnosus* CNCM 14036 and 15.5% for *L. paracasei* CNCM I-4034) than the other bacteria such as *Lactobacillus* rhamnosus GG, which is of the order of 5% on HT-29 cells (Dunne et al, 2001) (Table 3). Likewise, the Bifidobacteria, which is one of the objects of the present invention, *B. breve* CNCM I-4035, also adheres to said cells with a value much greater than 16.7% (FIG. 5) compared with 9% of the bacteria used as controls.

These data confirm the results of the present invention, showing the variability existing in the different probiotic strains. In this specific case, the lactobacillus controls present adhesion (4%) corresponding to half that of the bifidobacteria controls (8%), however, the isolated strains in the present invention present greater adhesion than their controls because when the 16s rRNA of the different groups were aligned, the ones with the best values for epithelial adhesion were selected.

Thus, in the case of *lactobacillus* the strains which presented adhesion of the order of 7.48 and 11.55% with respect to 4.80 and 4.09% for their controls (FIG. 3) were selected, and in the case of bifidobacteria those which presented adhesion of 16.7%, with respect to 8.8 and 9.1% of their controls (FIG. 6) were selected. In other words, the bacteria making up the different objects of the present invention has a greater capacity of colonizing and remaining in the intestine and will therefore lead to a better probiotic effect.

Results of the Characterization of the Isolated Bacteria 16s RNA Study

Different molecular techniques have emerged for the identification, composition and enumeration of the entire bacterial community of the intestine, most of which are based on the study of 16s ribosomal RNA gene (rRNA), because in the past decade the 16s rRNA gene has revolutionized the way that taxonomists classify and identify bacteria. The 16s rRNA gene comprises regions ranging from highly variable to highly conserved, and the difference of sequences are used for determining the phylogenetic relationships and distinguishing bacteria from species to strains. There are databases available with more than 200,000 16s rRNA genes, such as for example NCBI/BLAST (http://blast.ncbi.nlm.nih.gov/Blast.cgi), ribosomal database project-RPD (http://rpd.c-me.msu.edu/htlm) and EMBL (http://www.embl-heidelberg.de/), these databases compare the existing sequences of the 16s rRNA gene with new sequences obtained. As shown in Example 2, the isolated strains in the present invention presented high homology with *Lactobacillus rhamnosus*, *Lactobacillus paracasei* and *Bifidobacterium breve*, which is consistent with the background documents stating that in a child fed with breast milk there are high levels of bifidobacteria in faeces, between 40-60% of the total of the microbiota, where *Bifidobacterium breve* is found in a considerable percentage (Harmsen et al. 2000). There is also a high percentage of *lactobacillus*, mainly *L. casei*, *L. paracasei*, *L. acidophilus*, among others (Heiling et al. 2002, Satokari et al. 2002).

The percentage of homology of the 16s rRNA gene of the isolated strains was very high (99-100%) according to the NCBI/BLAST database (Example 2). The fragments of the 16s rRNA gene are approximately 1.4 kb, and the secondary fragments range between 1474 by for *Lactobacillus rhamnosus* 22A HERO (CNCM I-4036), 1274 by for (CNCM I-4034)7 HERO and 1118 by for *Bifidobacterium breve* 15B HERO (CNCM I-4035). Precisely the latter presents homology of 100% with *Bifidobacterium breve* ATCC 15700 and a non-cultivable clone of *Bifidobacterium,* therefore amplifying the sequenced fragment of the 16s rRNA gene would be of interest, but in this case a larger fragment could not be obtained because the oligonucleotides 27F (SEQ. ID. NO 1) and 1492R (SEQ. ID. NO 2), which amplify a fragment of approximately 1400 bp, were unable to amplify the 16s rRNA gene of the *Bifidobacterium breve* 15B HERO strain (CNCM I-4035). Therefore, other universal oligonucleotides which amplify smaller fragments such as 39F (SEQ. ID. NO 3) and 1391R (SEQ. ID. NO 4) were used.

The sequenced fragments of the 16s rRNA gene of the isolated *lactobacillus* strains show a homology of 99% with a group of *Lactobacillus rhamnosus*, and the other strain presents a homology of 100% with a large variety of *Lactobacillus paracasei*, and with a small number of *Lactobacillus casei*. The fragments of 16s rRNA of the controls, of the *Lactobacillus rhamnosus* 22A HERO (CNCM I-4036) and *Lactobacillus paracasei* 7 HERO (CNCM I-4034) strains, and a fragment of *L. paracasei* which had a high homology with the isolated strain were aligned. From this, it can be observed that there is a difference of 4 bases between the control strains, *L. rhamnosus* 22A HERO (CNCM I-4036) and *L. paracasei* 7 HERO (CNCM I-4034). There is also a difference of 4 bases between the LGG and *L. casei* controls. The *Lactobacillus rhamnosus* 22A HERO strain (CNCM I-4036) presents a difference of 1 base with both controls, a difference of 1 base with the LGG control and a difference of 3 bases with *L. casei*. In this case, there are few differences between the aligned strains, which would indicate that in these strains the 16s rRNA gene is fairly conserved.

In order to broaden the genomic information of the studied bacterial strains, the intergenic space present between the 16s and 23s genes was amplified, this space being known for having a large size variability (Barry et al. 1991 & Navarro et al. 1992), and it was also used for differentiating species of prokaryotes (Barry et al. 1991). In the isolated strains the fragments of the intergenic space range in length between *Lactobacillus rhamnosus* 22A HERO (CNCM I-4036) 579 bp, *Lactobacillus paracasei* 7 HERO (CNCM I-4034) 512 by and *Bifidobacterium breve* 15B HERO (CNCM I-4035)182 bp. The 16s-23s intergenic fragments were compared with those in the NCBI/BLAST database, and the results show a homology of 100% for the *Lactobacillus rhamnosus* 22A HERO strain (CNCM I-4036) with isolated *Lactobacillus*

*rhamnosus* TS1 and *Lactobacillus rhamnosus* PS1 16S. When comparing the homology results shown for 16s rRNA, the results are completely different, therefore it is possibly a strain that is not in the database or that the NCBI/BLAST database has more information about 16s rRNA and not about the 16s-23s intergenic space. These results indicate that the isolated bacteria object of the invention is unique, which has been confirmed by the Pasteur Institute when specifically giving it the name *Lactobacillus rhamnosus* CNCM I-4036.

In the case of the *Lactobacillus paracasei* 7 HERO strain (CNCM I-4034), the results of the 16s-23s intergenic space show a homology of 100% for *Lactobacillus casei* ATCC 334. The NCBI/BLAST database contains the complete genome and it is on the list of *L. casei* showing a homology of 100% for the 16s rRNA, therefore it is very probable that the isolated strain is *L. casei* ATCC 334; in any case when sequencing other fragments of the genome, such as the 23s or 5s genes or others, they could ratify or discard the idea that it corresponds exactly to this strain. In this sense, after the pertinent analyses, the Pasteur Institute has acknowledged the strain as unique.

For the case of the bifidobacteria strain, the fragment is rather small, therefore the intergenic space of the controls was amplified, giving 165 by for *Bifidobacterium longum* and 298 by for *Bifidobacterium bifidum*, which ratifies the existence of a large variation in the size of the fragment. The control strains, the isolated strain, *Bifidobacterium breve* 15B HERO (CNCM I-4035), and the strain which showed a homology of 99% (NCBI/BLAST) with the strain of the invention were aligned, observing a large difference between the controls and the *Bifidobacterium breve* strains; however, there is a difference of only one base between the strain of the invention and the strain presenting a homology of 99% (*Bifidobacterium breve* 16S-23S internal transcribed spacer (ITS), strain Y8). This strain is completely different from the strain with a homology of 100% for the 16s rRNA, therefore it could be a strain that is not entered in this database.

All these results demonstrate that the three isolated strains in the present invention are new, as they have not previously been described in the state of the art.

Phenotypic Identification

As shown in Example 11, the present used a carbohydrate fermentation kit (API 50CH) (FIG. 8) and an enzymatic activity kit (API Zym) (FIG. 9) to analyze the biochemical capacities of the isolated species. They constitute a rapid and theoretically reproducible method for the phenotypic identification of pure bacterial cultures. These tests have been used for characterizing and identifying lactobacillus in milk (Medina et al. 2001), yoghurt and other fermented dairy products (Andrighetto et al. 1998), and cheeses (Andrighetto et al. 1998, Bouton et al. 1998 and De Angelis et al. 2001). However, the reliability of these tests has been questioned, especially for API 50CH, because it was initially developed to identify lactobacillus strains for clinical use, and because the manufacturer's database has not been updated for some lactobacillus species, showing ambiguous results for identification (Andrighetto et al. 1998 and Collins et al. 1993), however, the information offered is valuable for phenotypically characterizing the isolated strains.

As observed in FIG. 8, the isolated strains as well as the controls present low proteolytic activity functioning as trypsin and α-chymotrypsin, although they presented activity that was different from leucine, for valine they present minimal activity in bifidobacteria and very high activity in lactobacillus.

Bifidobacteria also present high activity for α and β-galactosidase and for α-glycosidase. The α-galactosidase and α-glycosidase activity could differ from the bifidobacteria of other lactic acid bacteria, as described by Desjardins et al. (1990).

It is observed that in bifidobacteria and in the isolated *Lactobacillus rhamnosus* 22A HERO strain (CNCM I-4036) there is high α-galactosidase activity. In other words important activity because the hydrolysis of specific sugar such as α-D-galactosyl-oligosaccharide allows selective proliferation of bifidobacteria in the intestinal tract (Gopal et al. 2001; Gulewicz et al. 2002) because bifidobacteria can use galactooligosaccharides. The evaluation of the phenotypic characteristics of bifidobacteria has allowed confirming their prior classification by genetic means and determining that their enzymatic actions allow using several hydrocarbon substrates, preferably glucose polymers with α bonds for the production of lactic acid.

It has been described that few strains of other origins and genera, including lactobacillus, present β-glucuronidase capacity (Gopa et al. 2001; Hopkins et al. 1998). Thus, the lactobacillus and bifidobacteria strains of the present invention as well as their controls do not present levels of β-glucuronidase activity, which is interpreted as a favorable characteristic. The lack of β-glucuronidase activity is a characteristic that all the probiotics considered to be good must have because this enzyme is produced by faecal enzymes (nitroreductase, azoreductase) of a microbial origin, which cause pro-carcinogens to turn into carcinogens (Kurman 1988). Nanno et al. (1986) demonstrated that extracts of positive β-glucuronidase bacteria increase the mutagenic activation of biliary metabolites of benzopyrene, whereas extracts of negative β-glucuronidase do not present this activity. In summary, it can be said that since these bacteria present low activity to other carbon sources such as mannose, fucose and glucuronides, they prefer lactose and glucose as carbon sources for metabolism, although the isolated *Lactobacillus rhamnosus* 22A HERO strain (CNCM I-4036) presents enzymatic activity for α-fucose, which entails a favorable effect on the fermentation of fucosyl-lactose derivatives like those present in breast milk, having a known favoring effect on the growth of bifidobacteria. This property means that the probiotics of the present invention have a very particular application in infant diets, although they can also be applied in adult diets and special diets.

Another aspect that should be mentioned is the result of API 50CH (FIG. 9B), where the *Lactobacillus paracasei* 7 HERO strain (CNCM I-4034) ferments inulin, a capacity that its controls do not have. The capacity of fermenting inulin is not a common property among lactobacillus (Cebeci and Gurakan 2003; Makras et al. 2005). This indicates that the strain of the invention has the capacity to ferment fructo-oligo-saccharades (FOS), widely used as prebiotics, in infant diets, promoting the development of intestinal microbiota in which *lactobacillus* and bifidobacteria predominate. This characteristic of the bacteria of the invention reinforces the fact that the probiotics of the present invention have a very particular application in infant diets, although they can also be applied in adult diets and special diets. The capacity of inulin and FOS in increasing the number of bifidobacteria in the colon has been demonstrated (Roberfroid et al. 1998; Van Loo et al. 1999).

Probiotic Activity

Once the aforementioned requirements concerning resistance to pH, resistance to bile salts, adherence to intestinal epithelial cells and sequencing 16S have been met, the isolated and defined probiotic microorganism is had. The next step consists of characterizing its probiotic activities, specifically, it would be necessary to characterize the probiotic properties of *Lactobacillus rhamnosus* HERO 22A (CNCM I-4036) and/or *Lactobacillus paracasei* HERO 7 (CNCM I-4034) and/or *Bifidobacterium breve* HERO 15B (CNCM I-4035).

Taking into account that the bacteria of the invention meet the requirements of a probiotic in relation to resistance to pH, bile salts and adherence, said bacteria can be applied in different areas in which the use of probiotics is known in the State of the Art, among others, in the treatment and prevention of different pathologies such as lactose malabsorption, reduction of cholesterol plasma levels, different types of diarrheas, inflammatory bowel diseases, cancer, disorders caused by pathogenic bacteria, etc. Thus, said probiotics will be applicable in different fields, like in the action on the main digestive pathogens and in the stimulation of the immune system, among others.

Pathogenic Bacteria

Among the different types of studies conducted on the probiotics, those involving pathogenic bacteria of the gastrointestinal system are of special interest. When choosing pathogenic bacteria, their mechanism of pathogenicity, which varies from one to the other, must be taken into account. A bacteria of interest is enterotoxigenic *Escherichia coli* because the production of its enterotoxin is an important cause of diarrhea in humans. Recent studies have described that certain lactic acid bacteria have an antagonistic effect with respect to enterotoxigenic *Escherichia coli* (Gopal et al. 2001; Todoriki et al. 2001; Chu et al. 2005; Tsai et al. 2007) and with respect to other pathogenic bacteria such as *Salmonella typhimorium* and *Shigella flexneri* (Tien et al. 2006; Jankowska et al. 2008).

Another aspect of interest of the probiotic strains is the possible production of substances called bacteriocins, which are secreted by some bacteria in order to compete with other microorganisms growing in the same niche. These substances can inhibit the growth or adhesion of pathogenic bacteria on intestinal epithelial cells, which can be produced by some lactic acid bacteria (Klaenhamer 1993; Jack et al. 1995; Sablon et al. 2000).

An important aspect is to know the interaction of the probiotic or pathogenic bacteria with the intestinal epithelial cells because all the bacteria present in human microbiota directly interact with them.

It has been described that the presence of pathogenic bacteria in intestinal epithelial cells stimulates a pro-inflammatory response profile (Th1), releasing cytokines such as TNF-α and IL-8, activating NF-κB, (Tien et al. 2006; O'Hara et al. 2006) and increasing their expression. This response in most cases is partially reduced in the presence of a probiotic bacteria, which would indicate a beneficial effect (Servin 2004).

Thus, some probiotics could modulate the properties of the DC, including their capacity to activate a specific immune response (Kelsall et al. 2002). A stimulation and tolerance equilibrium after contact with probiotic bacteria in the intestine could be important for maintaining their homeostasis and being able to carry out their beneficial protection functions with respect to pathogenic bacteria in the digestive system of the host.

The probiotic strains of the present invention shows to have an inhibitory effect on the growth of intestinal pathogenic microorganisms, such as pathogenic bacteria, among others, *Helicobacter pylori, Listeria monocytogenes, Shigella sonnei,* enterotoxigenic *Escherichia coli,* enteropathogenic *Escherichia coli,* enteric *Salmonella,* as well as enteric viruses, such as *Rotavirus*.

Lactose Malabsorption

Mammals are born with sufficient lactase activity for using lactose from breast milk. After weaning, this activity is gradually reduced with age, and the intake of food containing it leads to signs and symptoms related to lactose intolerance (abnormal increase of gas, abdominal pain, diarrhea, etc.). It is known that the use of probiotics releasing lactase favors the digestion of lactose in the lumen of the intestine, fighting the symptoms of lactose intolerance.

Reduction of Cholesterol Levels

The high level of blood lipids, such as cholesterol and triglycerides, implies a high risk to human health due to the association thereof with heart disease. Since the consumption of foods with a low fat content or with microorganisms participating in lipid metabolism is very beneficial for preventing these conditions, lactobacillus strains regulating serum lipids have been characterized. This probiotic effect is closely related to the hydrolysis of bile salts.

It has thus been observed in different studies in animals (Akalin et al. 1997; Fukushina and Nakano 1996) and in humans (Lin et al. 1989) that the administration of probiotics can reduce serum cholesterol concentration.

Diarrhea

It is a fact that the best documented clinical application of a probiotic is the treatment of acute diarrhea. Clinical trials have shown efficacy of the use of probiotics in the treatment for the prevention and/or treatment of several intestinal disorders including antibiotic-induced diarrhea (McFarland et al. 1995), diarrhea in adults (Höcter et al. 1990), children (Cetina-Sauri and Sierra 1994) and traveler's diarrhea (Kollaritsch et al. 1993).

In these cases, the probiotic used as a biotherapeutic agent affects the expression and the activity of a large number of enzymes and proteins, regulating the intestinal epithelium and possibly microbiota.

In relation to the antibiotic-associated diarrhea, taking probiotics when an antibiotic is prescribed can reduce the onset and/or shorten the duration of the diarrhea. The most widely used microorganisms are: *Enterococcus faecium* SF6 (Wunderlich et al. 1989), *Lactobacillus* GG (Siitonen et al. 1990; Vanderhoof et al. 1999), *Lactobacillus acidophilus, L. bulgaricus,* and *Saccharomyces Boulardii*. These agents contribute to reducing the alteration of the microbiota in the intestine, the change in the consistency of the stools and the frequency of the latter.

Diarrhea caused by *Clostridium difficile*, which is an opportunistic pathogen that takes advantage of the alteration of the intestinal microbiota due to taking antibiotics, presents a broad spectrum of clinical symptoms, ranging from mild benign diarrhea to intense colitis with the development of toxic megacolon, intraabdominal and systemic complications that can lead to patient death. Diarrheas usually occur a few weeks after beginning antibiotic therapy. The pathogenic sequence begins with an alteration of the intestinal bacterial microbiota induced by antibiotics, which allows colonization by *C. difficile* if the person is exposed to the intake of this agent. Subsequently, the bacteria releases toxins causing tissue damage. The pathogenic strains of *C. difficile* produce toxins called A and B. *S. Boulardii* inhibits toxins A and B by releasing a 54 kDa protease which cuts out these toxins and their membrane receptors (Castagliuolo et al. 1999).

It has been seen that the oral administration of *Lactobacillus rhamnosus* GG and *Saccharomyces boulardii* has been effective in restoring the normal microbiota in patients.

Traveler's diarrhea is due to a bacterial, viral or parasitic infection. There are many microorganisms causing it and they are probably different from one country to another. By frequency, they include: *E. coli, Shigela, Salmonella, Campylobacter, Rotavirus* and *Giardia lamblia*. Traveler's diarrhea affects half the travelers going to high-risk areas. The bacteria used as probiotics in different studies are: *Lactobacillus, Bifidobacterium, Streptococci* and *Enterococci. Lactobacillus GG* has been the most effective probiotic with respect to traveler's diarrhea.

Inflammatory Bowel Diseases

One of the main uses of probiotics involves an imbalance in the microbiota and immune system. According to this interest, the study of inflammatory bowel diseases is one of the most interesting focal points for the possible use of probiotics as clinical therapies. The studies conducted in this area have provided important information on the clinical use of probiotics and the gene expression of different intermediaries involved in these diseases.

Inflammatory bowel diseases (IBD) are chronic inflammatory disorders of the intestine with unknown origin (ulcerative colitis, Crohn's disease), the pathogenesis is complex and involves at least 3 important elements: genetic susceptibility factors, enteric microflora and immunity-mediated damaged. It has been hypothesized that IBDs occur due to an abnormal response of the T cells with respect to the microbiota, it has also been speculated that the presence of pathogenic organisms could cause these diseases.

There is a reduced level of *Lactobacillus* and *Bifidobacerium* in colon biopsies in patients with IBD (Fabia et al. 1993; Favier et al. 1997). Conventional treatments for IBD focus on suppressing or modulating the immunity of the host, and among these treatments, the use of antibiotics is an effective treatment for Crohn's disease. This would indicate that the use of probiotics for modifying microflora may be important in the treatment of IBD.

There is a recent study in the background in which it has been found that patients with Crohn's disease have reduced amounts of β-galactosidases in faeces during the active periods of the disease. This reduction is correlated with the reduction of *Bifidobacteria*, which are the source of β-galactosidase (Favier et al. 1997).

Cancer

Colorectal cancer is one of the most serious complications of IBDs, including ulcerative colitis and Crohn's disease (Eaden et al. 2001). The precise mechanism whereby IBD can generate a carcinogenic process is not well understood. It is assumed that it could be the cause of a chronic inflammatory process (Weitzman & Gordon 1990), which in some experimental models may function as a tumor promoter.

The intestinal microbiota and the immune system play an important role in regulating carcinogenesis. Probiotics can have an effect in both, hence great effort has been made in this field to act against colon cancer. It has been found that probiotics can reduce the concentrations of enzymes, mutagens, secondary bile salts which are possibly involved in the carcinogenic process of the colon (Wollowski et al. 2001). Epidemiological data supports that the daily consumption of fermented products has a protective effect against colon adenomas or cancer (Rafter and Glinghammar 1995).

A symbiotic combination has been used for the study of the prevention of cancer, which is a mixture of a probiotic and a prebiotic. This combination increased short-chain fatty acid levels, which are the main products of bacterial fermentation, their primary role being to act as a source of nutrients for the intestinal epithelium. They are associated with an induction of differentiation, suppression of proliferation and increase of in vitro apoptosis (Heerdt et al. 1997; Medina et al. 1997), and they may play a role in preventing some diseases such as gastrointestinal disorders and cancer (Julia et al. 2006).

The present invention not only demonstrates the capacity of the selected strains for inhibiting the growth of pathogenic bacteria and intestinal enteric viruses, but it also demonstrates superior characteristics which define the probiotic properties of microorganisms, such as resistance to pH, bile salts and adherence to the intestine, in comparison with control probiotic bacteria known in the state of the art.

The results have shown in all cases that the probiotic properties of the bacteria of the invention are better than said control bacteria. It is thus known that the activity of the bacteria used as controls is focused on the following

*L. casei* Inmunitas of Danone

The beneficial effects associated with probiotic compositions containing *L. casei inmunitas* (Actimel®) have the best immune response to different infectious agents, increasing the level of activating cytokines of the immune system, improving the proliferative response of T cells and modulating the expression of NK cells. It has been observed that drinking Actimel® improves the prognosis of infant diarrheas associated with infections, reducing the severity and duration thereof.

The compositions containing *L. casei inmunitas* in turn have positive anti-inflammatory effects on the mucosa of the human colon because they increase the immune response of the host, which is beneficial for individuals with inflammatory bowel diseases and for preventing colon cancer.

In view of the foregoing and of the different comparative experiments conducted which have shown better probiotic properties of *Lactobacillus paracasei* HERO 7 (CNCM I-4034) with respect to *L. casei inmunitas, Lactobacillus paracasei* HERO 7 (CNCM I-4034) has an excellent application, among others, in preventing different pathologies such as lactose malabsorption, reduction of cholesterol plasma levels, different types of diarrheas, inflammatory bowel diseases, cancer, etc., in the improvement of the immune response with respect to different infectious agents, in the improvement of infant diarrheas, as an antiinflammatory of the mucosa of the human colon (and accordingly in preventing colon cancer).

LGG

*Lactobacillus* GG adheres to the intestinal cells, stimulating the immune response and preventing pathogenic diarrhea. Different studies have demonstrated that the consumption of compositions containing LGG, such as Bioactif of Kaiku®, inhibits the competitive colonization of the intestine by pathogenic microorganisms. These microorganisms in turn produce antimicrobial compounds inhibiting the growth of pathogenic strains, with the subsequent inhibition of the growth of pathogenic strains. Thus, the consumption of compositions with LGG maintains or restores intestinal microflora equilibrium, optimizing absorption processes of the function of the intestinal mucosa.

In view of the foregoing and of the different comparative experiments conducted which have shown better probiotic properties of *Lactobacillus rhamnosus* HERO 22A (CNCM I-4036) with respect to *Lactobacillus* GG, *Lactobacillus rhamnosus* HERO 22A (CNCM I-4036) has an excellent application, among others, in stimulating the immune response and preventing pathogenic diarrhea and maintaining or restoring the intestinal microflora equilibrium.

*Bifidobacterium Longum* and *Bifidobacterium bifidum*

It is known from the state of the art that *Bifidobacterium Longum* are resistant to antibiotics, therefore their consumption in periods in which individuals are being treated with antibiotics prevents the diarrhea that is occasionally caused in patients. Other applications of these microorganisms are aimed at reducing cholesterol, alleviating the symptoms of lactose intolerance, stimulating the immune system and preventing cancer.

The consumption of compositions with *B. bifidum* alleviates the symptoms associated with diarrhea. In turn, they are microorganisms which increase the immunological response of the individual by increasing phagocytic activity in peripheral blood.

In view of the foregoing and of the different comparative experiments conducted which have shown better probiotic properties of *Bifidobacterium breve* HERO 15B (CNCM I-4035) with respect to *Bifidobacterium Longum* and *B. bifdum*, *Bifidobacterium breve* HERO 15B (CNCM I-4035) has an excellent application, among others, in stimulating the immune response and preventing diarrhea caused by antibiotics, in reducing the cholesterol, improving the symptoms of lactose intolerance, in preventing cancer, etc.

Probiotics in Foods, Drinks, Drugs, etc.

Incorporating viable microorganisms in foods is a long-standing practice. Yoghurt and other fermented milks are foods which have traditionally included live microorganisms. The development of functional foods in recent years has brought about the development of new applications based on the use of microorganisms capable of producing beneficial effects for the organism.

The area of infant diets has not been an exception in the field of the functional foods and ingredients of this type have started to be included in different types of infant foods in recent years. Probiotics have been one of the main lines of development, being applied mostly in the field of milk formulas, primarily continuation and growth formulas. The objective that is sought with the incorporation of probiotics in foods is their implantation in the colon of the host and the procurement of a series of beneficial effects (reduction of pathogenic flora, production of vitamins and other nutritional substances, reduction of the pH of the medium, etc.).

The probiotic bacteria of the present invention are all recognized as species comprised within the group of lactic acid bacteria, and they have been known for some time on an international level for their nil pathogenic power. Therefore, they are susceptible to being used for the fermentation of dairy products, among others, in an isolated manner or in conjunction with other lactic acid bacteria, for example *Streptococcus thermophilus, Lactococcus lactis, Streptococcus lactis*, etc. Likewise, their use in infant milk, like any another lactic acid bacteria, does not involve any potential food safety problem.

The incorporation of these probiotics in foods and beverages must assure a particular number of live bacteria in the final product after the maximum shelf-life period of the product by means of using a suitable mixing (or fermentation, where appropriate) process.

The probiotics of the present invention can be applied in infant diets as well as in adult diets and special diets. Said probiotics can be used in the form of powder alone or mixed with other excipients known in the state of the art such as sugar, proteins, milk powder, etc., or as active ingredients in the fermentation of preferably dairy-based products. Thus, said probiotics can be incorporated in powder or in liquid form in foods used by the general population, particularly milk and milk-derived products, especially fermented milk and cheeses; cereals and derivatives, including bread doughs; soups and other similar products in dehydrated form; fermented meat products; fruit derivatives, juices and soft drinks; foods for specific nutritional uses, including infant milk, infant cereals, ready-to-eat infant foods, etc. They can also be found in food supplements and special formulas for oral and enteral nutrition for clinical use. If it is in a powder product (infant milk, cereals . . . ), the probiotics will be incorporated by dry mixing them into the end product. Thus, the probiotics of the present invention can be incorporated in food powder intended for being reconstituted with water or another liquid such as milk (infant milk powder, cereals . . . ).

In their use for fermenting milk or dairy products and preparing acidified milk, the probiotics are added to the liquid milk base during an intermediate step of the process and producing fermentation at controlled temperature and time to obtain acidified milk.

The probiotics of the invention can also be applied in food supplements and even in pharmaceutical products, which could be presented in the form of powder preparations, tablets, sugar-coated tablets, etc. These products have a field of use in the treatment of inflammatory bowel diseases, gastric ulcers, acute diarrhea and other diseases of the gastrointestinal tract.

EXAMPLES

Example 1

Amplifying 16S-23S Intergenic Fragments

The intergenic segments of the selected strains were amplified, sequenced and the homology search was performed in the NCBI (BLAST) database which delivered the following results:

*Lactobacillus rhamnosus* 22A (CNCM I-4036) has a homology of 100% of a 579 by fragment with:
*Lactobacillus rhamnosus* isolate TS1
*Lactobacillus rhamnosus* isolate PS1 16S
*Lactobacillus paracasei* 7 (CNCM I-4034) has a homology of 100% of a 512 by fragment with:
*Lactobacillus casei* ATCC 334
*Bifidobacterium breve* 15B (CNCM I-4035) has a homology of 99% of the 182 by fragment 16s-23s intergenic space, with:
*Bifidobacterium breve* (ITS), strain Y8
*Bifidobacterium longum* (ITS), strain Y10

Example 2

Aligning Sequenced Sections

The Clustalw program on-line tool (http://www.ebi.ac.uk/clustalw/) was used to align the sequenced sections of the selected strains and controls.

The overall alignment of the sequences of rDNA 16S gene of the strains with the controls showed the existence of differences between the sequences of the controls and the samples *L. rhamnosus* 22A and *L. paracasei* 7, and a complete homology between the sample 7 and a selected sequence of *L paracasei* is observed.

Relating to the selected sample β. *breve* 15B, a difference between the sequences of the controls and the sample *B. breve* 15B, and a homology of 100% between *B. breve* 15B and a selected sequence of *B. breve* is observed.

The overall alignment of the sequences of the intergenic space 16S-23S of the strain 15B and controls allowed observing a large difference between the sequence of the controls and the sample *B. breve* 15B.

In fact the sequencing of the 16S-23S intergenic space is unique and does not coincide with anything described previously for a bifidobacteria which indicates that the strain of the invention is unique, an aspect recognized by the Pasteur Institute by giving it a denomination which is also unique.

Example 3

Taking and Processing the Samples

Taking of Samples.

Faeces from exclusively breast-fed children between 2 and 4 months old were taken in anaerobic conditions at the clinic of the pediatrician JM, the inventor of this patent. Parents were asked to bring their children to the clinic first thing in the morning, the children was expected to have a bowel movement after stimulation and after the bowel movement the faeces were collected in a sterile container by means of a plastic spoon which is adhered to its cover. Once the collection ended, the container with the sample was introduced in an anaerobic jar (Anaerojan®, Oxoid, Hampshire, United Kingdom) accompanied by a sachet generating anaerobic atmosphere (Anaerogen®, Oxoid, Hampshire, United Kingdom) and the jar was sealed hermetically and transported to the laboratory where the samples were processed in a time no longer than 2 hours.

Processing and Seeding the Samples

The samples to be analyzed can be handled once collected or prior to cooling at −80° C. in correctly identified Eppendorf tubes.

Thus, a suspension of 10% faeces in PBS (phosphate saline buffer (PBS, Sigma-Aldrich, Madrid, Spain)) and L-cysteine hydrochloride (Scharlau CEIME, Barcelona, Spain) (0.05%) is prepared. 7 dilutions from $10^1$ to $10^7$ are made from this preparation, finally 50 µl of each dilution are seeded in the two selected culture media and are incubated in anaerobiosis for culturing bifidobacteria (Anaerogen®) and $CO_2$ rich medium for *lactobacillus* ($CO_2$Gen) for 72 hours at 37° C.

Example 4

Preparing Culture Medium 3 specific culture media for bifidobacteria and a culture medium specific for *lactobacillus* are then indicated:

1. Beerens medium {Beerens 1990}: this medium is used to determine bifidobacteria.

For its preparation, in a one liter Erlenmeyer flask 47 g of Brain Heart Infusion Agar, 5 g of D-(+) Glucose, 0.5 g of iron citrate III, 0.5 g of L-cysteine and one liter of distilled water are mixed. This mixture is heated with constant stirring on a heated stirring plate for a couple of minutes until it boils, it is then left to cool at room temperature. Once 55° C. is reached, 5 ml of propionic acid and 2.2 ml of 2 Eq/L sodium hydroxide is added therein, then the pH is adjusted to 5.0.

2. BFM medium (Nebra & Blanch 1999): this medium is specific for bifidobacteria. Said medium has the following components, in the indicated proportions per liter of solution:

2 g meat extract
   7 g yeast extract
   2 g Starch
   0.5 g L-cysteine hydrochloride
   5 g sodium chloride
   5 g peptone
   2 g tryptone
   5 g Lactulose
   1 mg riboflavin*
   1 mg thiamine*
   16 mg methylene blue
   2 g lithium chloride
   5 ml Propionic acid
   15 g agar The corresponding amounts are used to prepare 500 ml of this bifidobacteria selective medium. This mixture is heated with constant stirring on a heated stirring plate for a couple of minutes until it boils, the solution is then autoclaved. Finally, the vitamins (*) are prepared in concentrated solutions (stock solution 1 mg/ml), they are then filtered and added together with the propionic acid to the culture medium when the solution reaches approximately 55° C.

3. Modified Columbia medium (pH 5.0): this medium is specific for bifidobacteria. Said medium has the following components in the indicated proportions per liter of solution:

Columbia Agar Medium (Oxoid, Hampshire, United Kingdom).
   Glucose (5 g/L).
   Cysteine (0.5 g/L).
   Agar (up to 15 g/L).

The previously indicated amounts are used to prepare 1000 ml of this bifidobacteria selective medium. The mixture is heated with constant stirring on a heated stirring plate for a couple of minutes until it melts, the solution is then autoclaved. Finally, the propionic acid is added to the culture medium when the solution reaches approximately 55° C. and the pH is adjusted to 5.0 with a 1N NaOH solution.

4. Rogosa agar medium: this medium is used to determine *lactobacillus*. For its preparation, the specifications supplied by the commercial company are followed.

It is prepared following the specifications supplied by the commercial company.

EXAMPLE 5

Seeding the Samples

Once the dilutions are performed, each of them is seeded in triplicate by means of an inoculation loop. All the plates with the different culture media are then incubated in a incubator with controlled temperature at 37° C.

The plates with the bifidobacteria culture media are previously introduced in anaerobiosis jars into which a sachet of Anaerogen® (anaerobic atmosphere generating system) is incorporated therein and in those containing the *lactobacillus* culture plates a sachet of CO2Gen® ($CO_2$ atmosphere generating system), they are finally incubated for 72 hours at 37° C.

Example 6

Determining the Number of Colony Forming Units

After the incubation, the dilutions having a growth greater than 10 colony forming units (CFU) are selected and the CFU in each of the media is counted through an electronic colony counter pen (Colony counter model 608702, Bio Co, Kobe, Japan). Finally, the total number of CFU is calculated by means of the following formula:

CFU=No. of colonies ×dilution factor ×dilution

Once the cultures are performed, the remaining faeces samples were stored at −80'C until performing the molecular biology studies.

Example 7

Determining the Resistance to pH and Bile Salts

After 72 hours of incubation, 100 colonies are selected from each of the culture media per child, taking into account the morphology observed with the naked eye. Said colonies both *lactobacillus* and bifidobacteria are incubated in liquid Man Rogosa Sharpe (RSM) medium and in anaerobic conditions for 48 hours. Subsequently, a stock of glycerol is immediately made from each of them (RSM+ Glycerol 10%).

At the same time as making the stocks of glycerol from the different colonies, their viability both at pH 3.0 and at a concentration of 3% bile salts (Oxgall, Sigma-Aldrich, Spain) are analyzed. To that end, the operation is performed in the following manner:
1. The colonies are centrifuged at 5000 rpm for 5 minutes.
2. The supernatant is removed and resuspended in sterile PBS.
3. Centrifuging again in the conditions similar to the above.
4. Steps 1 to 3 are repeated three times.
5. Finally resuspending in 1 ml of sterile PBS.
6. Inoculating 100 ml of the previous suspension in 900 ml of PBS at pH 7.0 and at pH 3.0 and 0.3% Oxgall dissolved in PBS.
7. Incubating in anaerobic conditions for 3 hours at 37° C.
8. Different dilutions ($10^1$ to $10^5$) are performed for each of the conditions in which the incubations have been performed.
9. Seeding 50 µl of each dilution.
10. Incubating 72 hours at 37° C. in anaerobiosis.
11. Determining by means of counting the number of colonies present both in the control and at pH and Oxgall.
12. Determining the viability of each colony by means of the quotient:

$$\text{Viability} = \frac{\text{No. of colonies at pH/Oxgall}}{\text{No. of control colonies}} \times 100$$

All those colonies showing a viability both at pH 3.0 and at 0.3% Oxgall greater than 90% are considered as positives, which colonies are kept to perform the rest of the tests. The other colonies are eliminated.

Example 8

Control Bacteria

The colonies used with positive controls were the following:
Para Bifidobacteria: *Bifidobacterium bifidum* and *Bifidobacterium longum* supplied by Hero Spain S. A.
Para *Lactobacillus:* 2 commercial *lactobacillus: Lactobacillus casei* (Danone®) and *Lactobacillus rhamnosus* GG (LGG) (KAI KU®) were used.

Once the initial screening with the selected colonies ended, a second screening was performed. In this case, the viability at pH 2.5 and 2.0 and at 0.5% and 0.7% Oxgall is verified. The protocol to be followed is similar to the one used in the first assay. Once the viability is determined, viability ranges are determined. In this second screening, the commercial bacteria controls presented values less than zero, therefore the one which had percentages of viability greater than 4% was determined as the initially optimal range for the selection of positive colonies. Dividing the colonies into 3 groups:
Group 1 Colonies with viability greater than 66%.
Group 2 Colonies with viability between 33 and 66%.
Group 3 Colonies with viability greater than the 4%.

FIGS. 1 and 4 show the results of resistance and survival to pH of the strains object of the invention. In the case of the strains *Lactobacillus rhamnosus* 22A (CNCM I-4036) as well as *Lactobacillus paracasei* 7 (CNCM I-4034), the results are illustrated in FIG. 1 and they demonstrate that at pH 3.0 the strains have a resistance similar or slightly greater than the commercially tested strains. Nevertheless, at pH 2.0, the strain 22A has a very high viability compared with the rest of the strains which do not survive that pH. In the case of the strain *Bifidobacterium breve* CNCM I-4035, the results are illustrated in FIG. 4, where it can be observed that at pH 3.0 the strain 15B shows a resistance significantly much greater than that of the other two bifidobacteria tested, its viability being greater than 100% which indicates that the bacteria can reproduced at this pH.

FIGS. 2 and 5 show the results of the influence of the bile salts on the survival of the strains of the present invention. In FIG. 2 the results related to the strains CNCM I-4036 and CNCM I-4034 are presented. As inferred, both strains show a percentage of survival much greater than the commercial strains tested, the percentage of survival being greater than 100% which indicates that they can even reproduce in the presence of these salts. In FIG. 5 the results related to the strain CNCM I-4035 are presented. As illustrated in this drawing, this strain shows a greater survival at higher concentrations if compared with the control bifidobacteria of the state of the art.

Example 9

Test of Adhesion to Intestinal Epithelial Cells

With the colonies already selected by the resistance to pH and bile salts, the cell adhesion assay is performed. Said assay has been performed with intestinal epithelial cells HT29. First, a series of attempts to determine the cell adhesion by means of different staining: Gram staining, methylene blue staining, giemsa staining, etc, was performed. Observing that it was very difficult to determine the percentage of adhesion to the HT29 cells through this means.

The question of which could be the best method to determine the percentage of adhesion was raised, the conclusion that the best method would probably be that which will allow recovering all the adhered bacteria being reached. Therefore the trypsinization method was chosen, and to that end it was proceeded in the following manner:
1. Incubating the HT29 cells at 37° C. and 5% $CO_2$ until confluence in 24-well plates.
2. Incubating the different colonies to be assayed in anaerobiosis.
3. Contacting the bacteria with the cells following the steps described below:
a. Centrifuging the bacteria at 5000 rpm for 5 minutes.
b. Removing the supernatant and resuspending the bacteria in 1 ml of sterile PBS.
c. Repeating steps a and b two more times.
d. Determining the O.D of each bacteria at 600 nm.
e. Diluting the bacterial culture to O.D of 0.8 in cell culture medium prepared previously without FBS (fetal bovine serum) and antibiotics (1 to $5 \times 10^6$ CFU/ml).
f. Removing the culture medium of the cells.
g. Washing several times with sterile PBS to remove the FBS and antibiotic residues.
h. Adding 250 ml of the bacterial suspension to each well. The experiment was performed in triplicate.
i. Incubating at 37° C. and 5% CO2 for 90 minutes.
4. Once the bacteria are incubated with the cells, the following is performed:
a. Removing the medium by aspiration with a pasteur pipette.
b. Washing 4 or 5 times with 1×PBS (pH 7.0).

c. Adding 100 μl of trypsin and incubating 10-15 minutes at 37° C.
d. Recovering the entire volume of the well and passing to an Eppendorf.
e. Washing the well with 150 μl of PBS and incorporating into the same Eppendorf.
f. Making several dilutions of each sample(4 or 5).
g. Seeding 50 μl of each dilution.
h. Incubating in anaerobiosis at 37° C. for 72 hours,
i. counting the number of colonies.
5. Determining the % of adhesion.

$$\% \text{ Ahesion} = \frac{\text{No. of adherent colonies}}{\text{No. of inoculated colonies}} \times 100$$

FIG. 3 shows the adhesion results of the strains CNCM I-4036 (strain 22A) and CNCM I-4034 (strain 7), object of the invention. Both strains have percentages of adhesion much greater than the percentages shown by the control strains, (in the case of the strain 22A, it is greater by two times), which indicates its potential action in modulating intestinal cell activities including the immunomodulation.

FIG. 6 shows the adhesion results of the strain CNCM I-4035 (strain 15B), also indicating a percentage of cell adhesion much greater than that of the control strains.

Example 10

Identifying Lactic Acid Bacteria

Isolating DNA, Amplifying and Sequencing of the 16S rRNA Fragment

Given the number of colonies selected in the adhesion test, their identification by means of amplifying the 16S rRNA fragment of each colony, sequencing and homology search in the National Center of Biotechnology Information (NCBI) database is directly performed.

First, the selected colonies are incubated in RSM medium for 48 hrs at 37° C. in anaerobiosis. The are then washed with PBS. To that end:
1. The colonies are centrifuged at 5000 rpm for 5 minutes.
2. The supernatant are removed and the bacterial pellet is resuspended in 1 ml of sterile PBS.
3. Repeating steps 1 and 2 three times.
4. Finally, resuspending the pellet in 1 ml of sterile PBS.

The Genomic DNA of the bacteria is then extracted, whereby it is performed in the following manner:
1. Centrifuging the previous suspension at 5000 rpm for 5 minutes and removing the supernatant.
2. The bacterial pellet is resuspended in 567 ml of Tris-EDTA (TE) buffer.
3. Adding 30 ml of 10% sodium dodecyl sulfate (SDS) and 3 ml of proteinase K (20 mg/ml).
4. Incubating the mixture at 37° C. for 1 hour.
5. Adding 100 ml of 5M NaCl and 80 ml of cetyl trimethylammonium bromide (CTAB)/NaCl.
6. Mixing and incubating at 65° C. for 10 minutes.
7. Adding the same volume (780 ml) of the chloroform/isoamyl alcohol (24:1) mixture.
8. Mixing and centrifuging for 5 minutes at 10000 rpm.
9. Extracting the upper aqueous phase and transferring to a new Eppendorf.
10. Adding the same volume of the phenol/chloroform/isoamyl alcohol (25:24:1) mixture.
11. Mixing and centrifuging for 5 minutes at 10000 rpm.
12. Extracting the upper aqueous phase and transferring to a new Eppendorf.
13. Adding 0.6 volumes of isopropanol.
14. Centrifuging for 13 minutes at 13000 rpm at 4° C.
15. Removing the supernatant and adding 1 ml of 70% ethanol to the precipitated DNA.
16. Centrifuging for 5 minutes at 13000 rpm at 4° C.
17. Removing the supernatant and the DNA precipitate, then leaving it to dry at room temperature.
18. Resuspending between 20-50 ml of water.
19. Measuring the concentration by means of spectrophotometer at 260 nm and obtaining the ratio 260/280 to verify its purity.

Amplifying the 16s rDNA gene and 16s-23s intergenic space by PCR.
Oligonucleotides used:
To amplify the 16s rDNA gene, the following sets of universal oligonucleotides were used:

```
27F
                                    (SEQ. ID. NO. 1)
5'-AGAGTTTGATCMTGGCTCAG-3'
(M = A + C)

1492R
                                    (SEQ. ID. No. 2)
5'-TACGGYTACCTTGTTACGACTT-3'
(Y = C + T)
```

A fragment of approximately 1450 by is amplified at a hybridization temperature of 55° C., amplification time of 90 sec and 35 cycles.

```
39F
                                    (SEQ. ID. No. 3)
5'-TGGCTCAGRWYGAACGCTRG-3'
(R = A + G, W = A + T, Y = C + T)

1391 R
                                    (SEQ. ID. No. 4)
5'-GACGGGCGGTGWGTRCA-3'
```

A fragment of approximately 1350 by is amplified at a hybridization temperature of 52° C., amplification time of 90 sec and 35 cycles.

Furthermore bifidobacteria specific oligonucleotides were designed, these are:

```
Bif
                                    (SEQ. ID. No. 5)
250 bp F 5'-CTCGTAGGCGGTTCGTCG-3'

Bif
                                    (SEQ. ID. No. 6)
250 bp R 5--AACGGGCCCCACATCCAG-3'
```

A fragment of approximately 250 by is amplified at a hybridization temperature of 65° C., amplification time of 20 sec and 30 cycles.

To amplify the 16s-23s intergenic areas of *lactobacillus* bacteria and bifidobacteria, the following sets of oligonucleotides were used:

```
lactoF
                                    (SEQ. ID. No. 7)
5'-ACACCGCCCGTCACACCATG-3' lactoR
                                    (SEQ. ID. No. 8)
5-CCHSTTCGCTCGCCGCTACT-3'
(H = A + T, S = G + C)
```

Lactobacillus specific oligonucleotides. A fragment of approximately 600 by is amplified at a hybridization temperature of 65° C., amplification time of 30 sec and 30 cycles.

```
ISBif F
                              (SEQ. ID. No. 9)
5'-GGGATGCTGGTGTGGAAGAGA-3'

ISBif R
                              (SEQ. ID. NO. 10)
5'-TGCTCGCGTCCACTATCCAGT-3'
```

Bifidobacteria specific oligonucleotides. A fragment of approximately 240 by is amplified at a hybridization temperature of 60° C., amplification time of 30 sec and 30 cycles.

To amplify the 16s rDNA gene and the 16s-23s intergenic space, between 50-100 ng of DNA were loaded for a PCR with final volume of 50 µl, a denaturation temperature of 94° C. for 30 seconds was used in each cycle. It was then programmed according to the conditions of each set of oligonucleotides specified above.

The result of the amplification was verified in a 1.3% agarose gel, the samples were stained with ethidium bromide and they were viewed in an ultra violet transilluminator.

The amplifications which were negative were repeated, those which were positive were amplified with the GE healthcare kit: Ilustra™ GFX™ PCR DNA and gel Band Purification Kit following the manufacturer instructions. Once purified, the samples were resuspendended in 25 ml of water and the purification was confirmed by viewing in a new 1.3% agarose gel.

The samples were then brought to the DNA Sequencing Service of the Institute of Parasitology and Biomedicine "Lopez-Neyra" (CSIC).

Example 11

Identifying by Means of Fermentation Tests

The API ZYM and API 50 CHL (bioMerieux's) systems are used. The API ZYM system is a semi-quantitative method for measuring enzymatic activities. This system has 20 wells, 19 of which contain a dehydrated substrate for detecting the activity of 19 enzymes (FIGS. 7 and 8), a colorimetric result is obtained which is indicative of the degree of enzymatic activity and was measured into a scale of 0-5 in comparison with the control. API 50 CH strips and API CHL medium (bioMerieux's) which is a method for obtaining a fermentation profile of 49 carbohydrates (FIGS. 9 and 10) was also used. A colorimetric result is obtained, but in this case they are only classified as positive (+), negative (−), and intermediate (V) in comparison with the control. The control bacteria were used in all the tests.

Example 12

Evaluating the Antimicrobial Activity of the Strains
L. paracasei CNCM I-4034, B. breve CNCM I-4035 and L. rhamnosus CNCM I-4036

Study Strains and Culture and Storage Conditions

In the present study a total of 3 strains belonging to the genus Lactobacillus and Bidifobaterium (Table 1) have been analyzed.

TABLE 1

Strains used in the study and culture conditions.

| Species | Strain | Culture medium | Temperature | Aeration |
|---|---|---|---|---|
| L. paracasei | CNCM I-4034 | RSM | 37° C. | Anaerobiosis |
| B. breve | CNCM I-4035 | 0.05% RSM-cysteine | 37° C. | Anaerobiosis |
| L. rhamnosus | CNCM I-4036 | RMS | 37° C. | Anaerobiosis |

For these strains, their antimicrobial capacity with respect to bacterial digestive pathogenic agents {Helicobacter pylori, Listeria monocytogenes, Shigella sonnei, enterotoxigenic Escherichia coli, enteropathogenic Escherichia coli and Salmonella enterica) and virus (virus Ito, Wa and Va70) shown in Tables 2 and 3, has been evaluated.

TABLE 2

Strains of pathogenic microorganisms used

| | Species | | | |
|---|---|---|---|---|
| | Helicobacter pylori | Listeria monocytogenes | Shigella sonnei | Rotavirus |
| Strains | LMG 8775 | CECT 4031 | CECT 457 | Wa |
| | LMG 18041 | CECT 935 | CECT 4887 | Va70 |
| | LMG 19449 | CECT 911 | CECT 413 | Ito |

TABLE 3

Strains of pathogenic microorganisms used

| | Species | | |
|---|---|---|---|
| | enterotoxigenic Escherichia coli | enteropathogenic Escherichia coli | Salmonella enterica |
| Strains | CECT 434 | CECT 443 | CECT 443 |
| | CECT 501 | CECT 729 | CECT 725 |
| | CECT 515 | CECT 742 | CECT 4594 |

In the case of the bacteria, these were stored in a RSM solution added with 20% (w/v) glycerol by means of freezing at −80° C. The virus were stored frozen in MEM medium at −190° C.

Obtaining the Cell-Free Supernatant for the Study

To obtain concentrated supernatant for the different assays, the strains were cultured in liquid medium for 17 h and 24h in RSM medium (CNCM I-4034 and CNCM I-4036) or RSM added with 0.05% cysteine (CNCM I-4035) at 37° C. The supernatant of each of the strains was collected by centrifugation and it was lyophilized. The concentrate obtained was dissolved until obtaining a solution concentrated 10x, the pH was neutralized to a value of 6.0 and was sterilized by means of filtration through 0.22 µm. Aliquots from the neutralized and sterilized supernatant were stored frozen at -20° C. until their use.

Activity Assays in Liquid Medium with Respect to Bacterial Digestive Pathogens

To carry out the assays of inhibition in liquid medium, a modification of the Spinler et al. protocol (2008) was used. Briefly, in multi-well plates of 250 µl of volume the supernatants obtained were separately added in increasing (0.2% to 4%) percentages (v/v) to culture medium inoculated at 5% with overnight growth of each of the pathogens. The growth curves were obtained in a manner monitored by means of measuring of OD at 595 nm using the Multiskan 5 Ascent plate reader. From the results obtained in the different replicates, the inhibition exerted was quantitatively assessed in the form of percentage of inhibition of the growth with respect to the control without the addition of supernatant of the inhibitory strain.

Activity Assays in Liquid Medium with Respect to Viral Digestive Pathogens

The assays of the viral infection reduction from supernatant of the study strains were carried out according to the protocol published by Botic et al. (2007) with modifications for the adaptation thereof to the work to be performed in this project. In this case, to perform these assays the HT-29 human intestinal cell line was used.

Results of the Activity Assays in Liquid Medium with Respect to the Bacterial Digestive Pathogens: *Listeria monocytogenes*, *Shigella sonnei* and *Helicobacter pylori*

To assess the effect of the growth supernatants of the strains *L paracasei*, *L rhamnosus* and *B. breve*, neutralized and concentrated 10× growth supernatants of 17 and 24 h, respectively, were used.

Figure 10B:
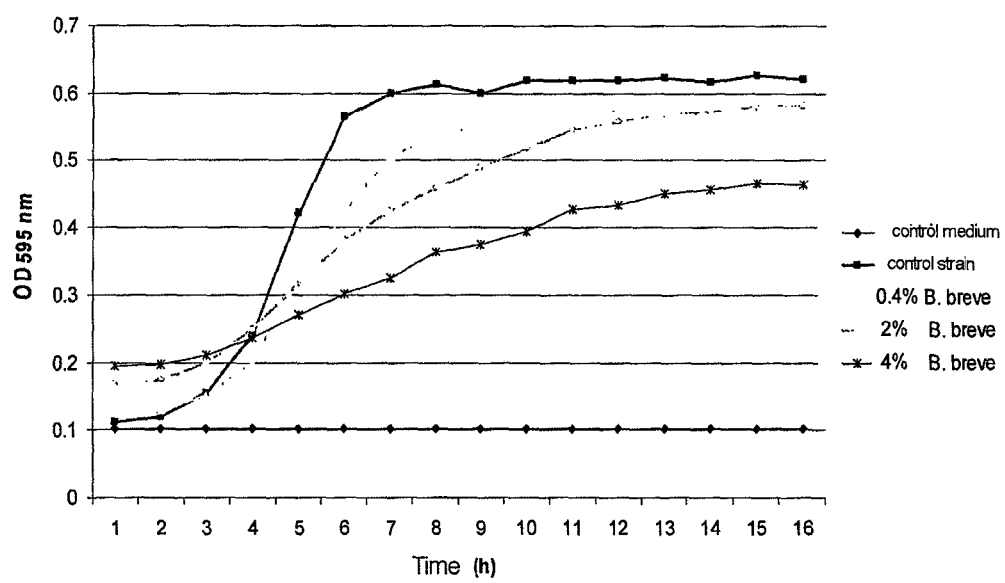
Figure 10C:
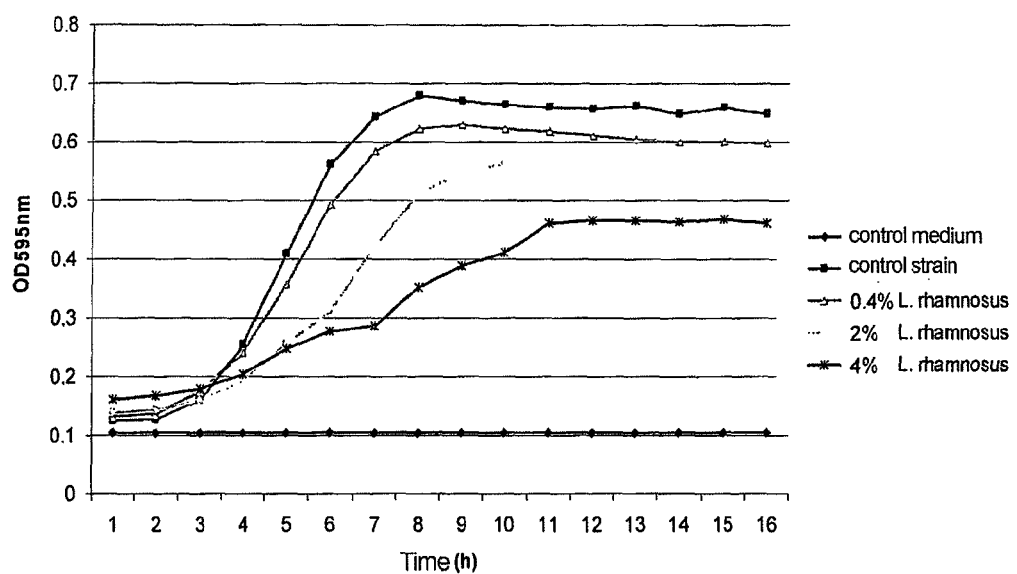

The results varied greatly depending both on the probiotic and on the pathogenic strain. In the case of *L. monocytogenes*, the addition of the supernatant obtained after the growth for 17 hours of *L. paracasei* had an inhibitory effect (FIG. 10A). In the case of *L. rhamnosus*, the best results were obtained from the addition of supernatant of 24 hours of culture. In the case of *B. breve*, the inhibition in *L. monocytogenes* CECT 4031 T (FIG. 10B) stood out. The results obtained for *S. sonnei* were similar to those of *L. monocytogenes*, since for *L. paracasei* the best results were obtained from the addition of the supernatant obtained after the growth for 17 h, and in *L. rhamnosus* the best results were obtained from the addition of supernatant of 24 hours of culture (FIG. 10C). In the case of *H. pylori*, a significant reduction in the growth of the pathogen from the supernatants of 17 h and 24 h of *L. paracasei* and *B. breve* has been obtained, the greatest inhibition being in the supernatants coming from 24 h of culture. The percentages of inhibition obtained are described in the following table (Table 4).

Results of the Activity Assays in Liquid Medium with Respect to the Bacterial Digestive Pathogens: *Salmonella typhi*, *Salmonella thyphimurium* and *Escherichia coli*

Figure 11:
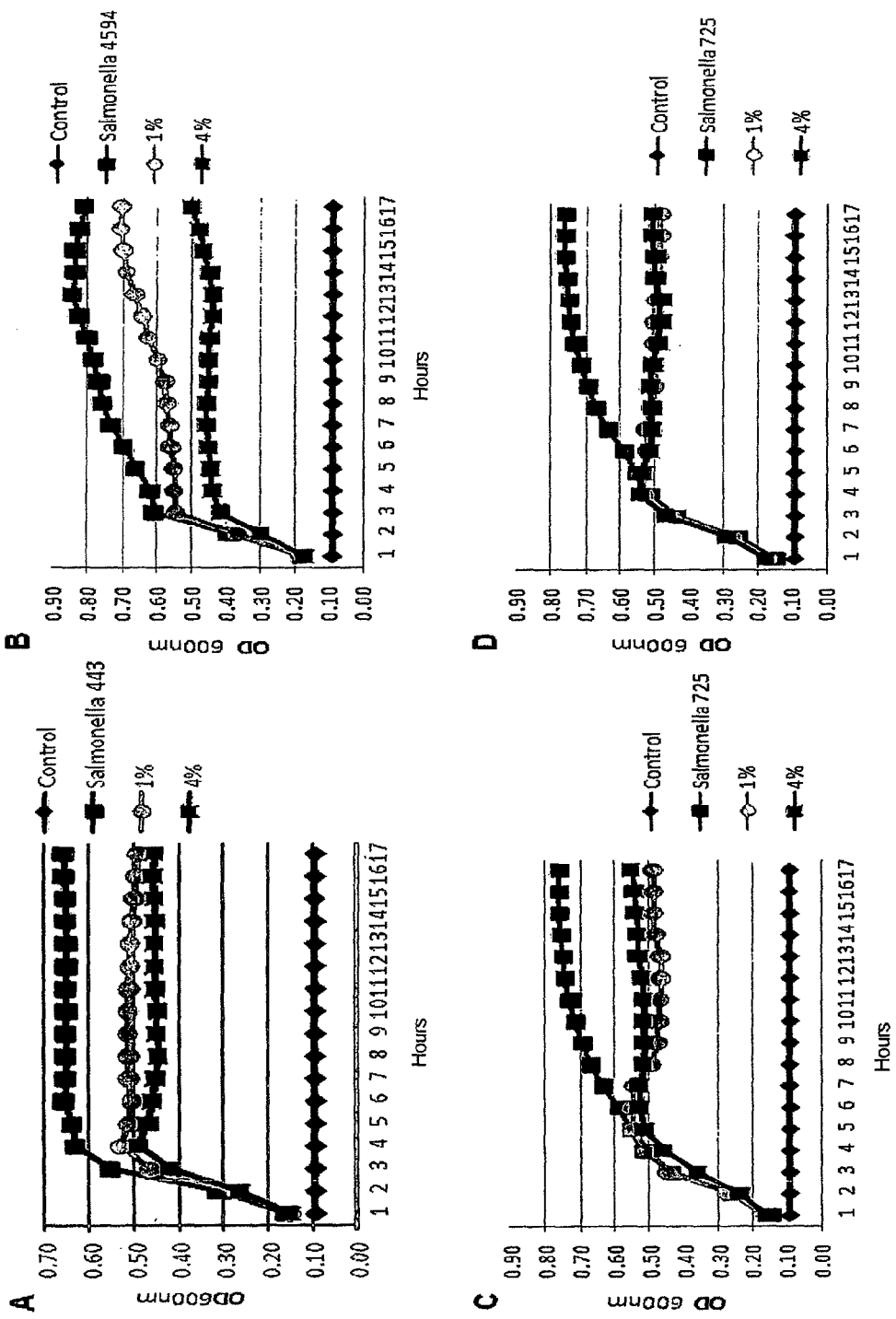
FIG. 11 shows the results of the inhibitory effects of the 1% and 4% neutralized and non-neutralized *Lactobacillus paracasei* CNCM I-4034 supernatant at 17 and 24h of culture time for the bacteria *Salmonella typhi* CECT 725, *Salmonella typhimurium* CECT 443 and *Salmonella typhimurium* CECT 4594. (A) inhibitory effect of non-neutralized *Lactobacillus paracasei* CNCM 1-4034 at 17h of culture time for the bacteria *Salmonella typhimurium* CECT 443. (B) inhibitory effect of non-neutralized *Lactobacillus paracasei* CNCM I-4034 at 24 h of culture time for the bacteria *Salmonella typhimurium* CECT 4594. (C) inhibitory effect of non-neutralized *Lactobacillus paracasei* CNCM 1-4034 at 24 h of culture time for the bacteria *Salmonella typhi* CECT 725. (D) inhibitory effect of neutralized *Lactobacillus paracasei* CNCM I-4034 at 24 h of culture time for the bacteria *Salmonella typhi* CECT 725. (E) inhibitory effect of non-neutralized *Lactobacillus paracasei* CNCM 1-4034 at 17 h of culture time for the bacteria Salmonella typhi CECT 725
Figure 11E:
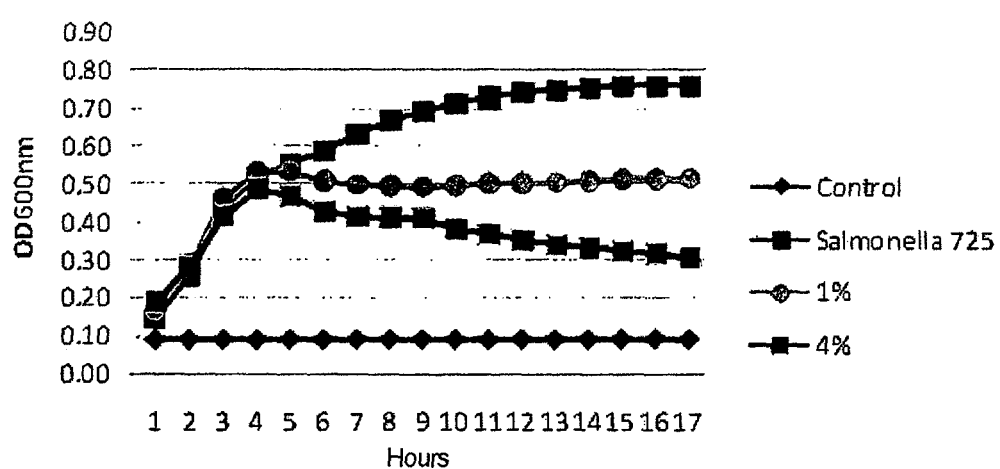

For the supernatant of the bacteria *L. paracasei*, a significant inhibition of the growth is observed for the *Salmonella* group tested (FIG. 11). This effect is mainly due to the non-neutralized supernatant, which suggests that it is due to the production of acid coming from the fermentation, limiting the pathogen growth. In the case of the *Salmonella typhi* CECT 725, the inhibitory effect either at 1% and 4% of the supernatant is observed regardless of whether this is neutralized or non-neutralized which suggests that the inhibition is due to some type of bacteriocin or other factor of unknown nature that would be exerting this effect on the pathogen.

Figure 12:
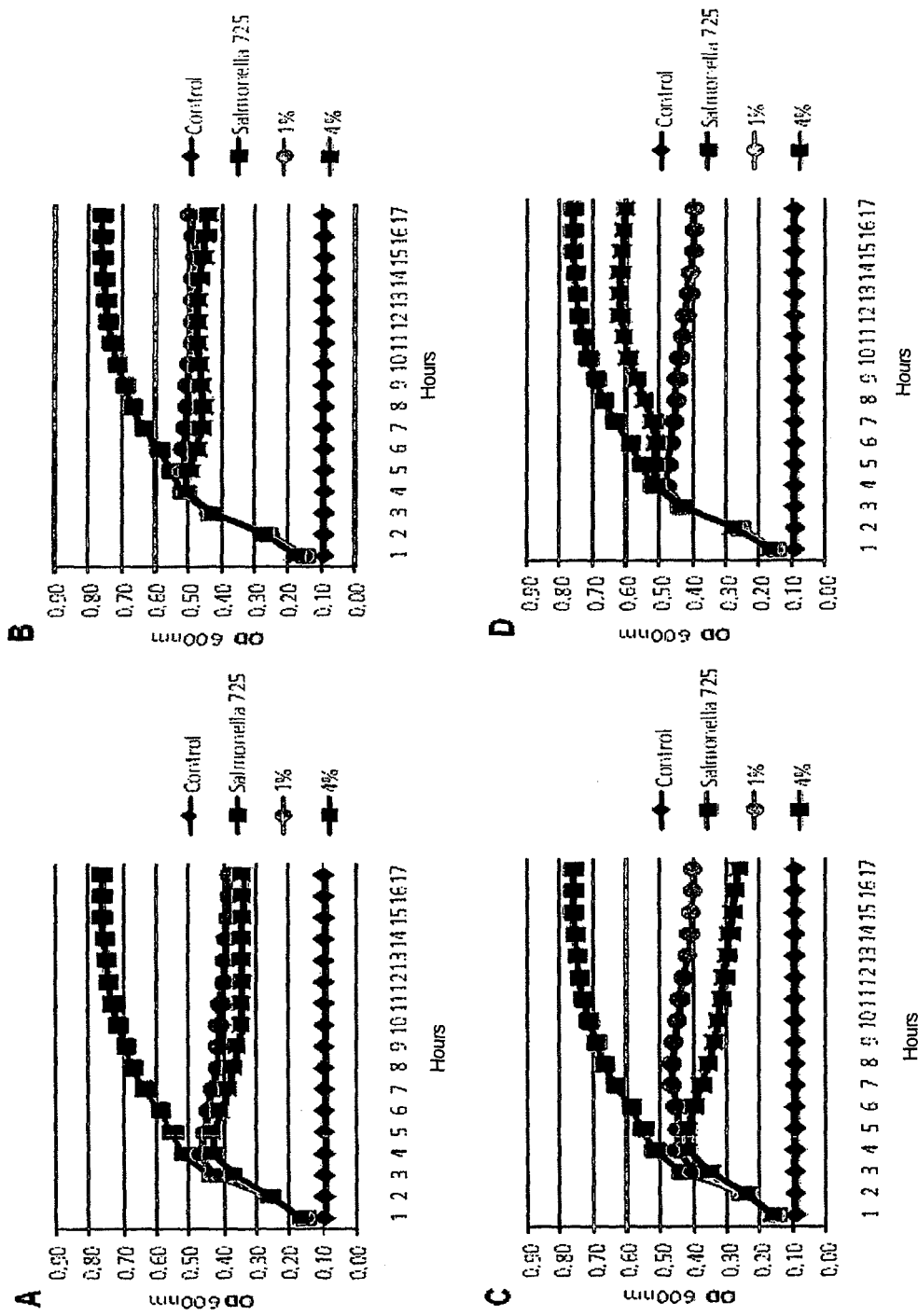
FIG. 12 shows the inhibitory effects of the 1% and 4% neutralized and non-neutralized *Bifidobacterium breve* CNCM I-4035 supernatant at 17 and 24 h of culture time for the bacteria *Salmonella typhi* CECT 725. (A) inhibitory effects of the 1% and 4% non-neutralized *Bifidobacterium breve* CNCM I-4035 supernatant at 17 h of culture time for the bacteria *Salmonella typhi* CECT 725. (B) inhibitory effects of the 1% and 4% neutralized *Bifidobacterium breve* CNCM I-4035 supernatant at 17 h of culture time for the bacteria *Salmonella typhi* CECT 725. (C) inhibitory effects of the 1% and 4% non-neutralized *Bifidobacterium breve* CNCM I-4035 supernatant at 24 h of culture time for the bacteria *Salmonella typhi* CECT 725. (D) inhibitory effects of the 1% and 4% neutralized *Bifidobacterium breve* CNCM I-4035 supernatant at 24 h of culture time for the bacteria Salmonella typhi CECT 725.

The supernatant of the bacteria *B. breve* exerts a growth inhibition on the bacteria *Salmonella typhi* (CECT 725). This effect is observed using the supernatant for all the conditions (17 and 24 h; neutralized and non-neutralized; 1% and 4%), the production of any type of bacteriocin or other factor of different nature (FIG. 12) again not being ruled out.

Figure 13:
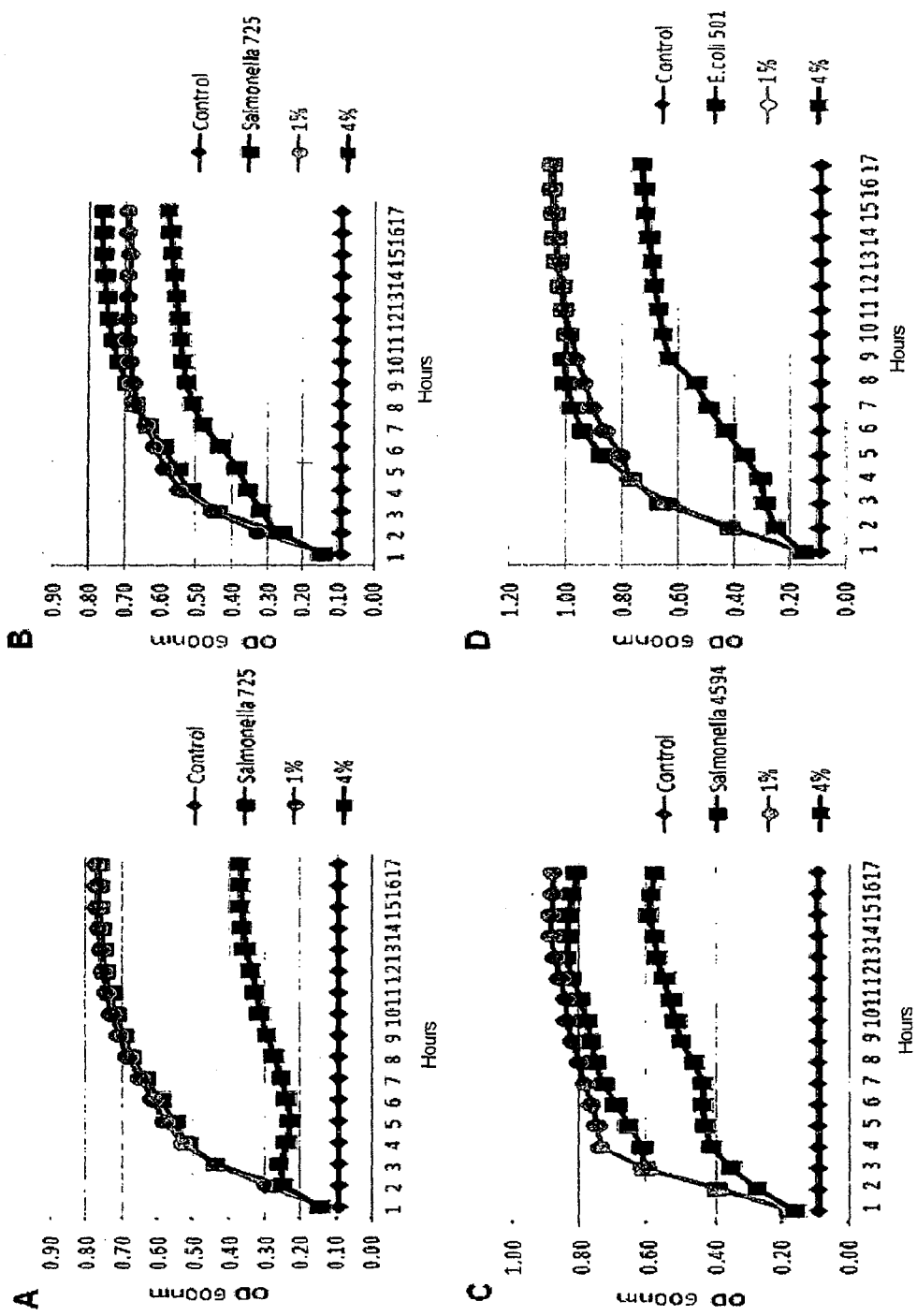
FIG. 13 shows the inhibitory effects of the 1% and 4% neutralized and non-neutralized *Lactobacillus rhamnosus* CNCM I-4036 supernatant at 17 and 24 h of culture time for the bacteria *Salmonella typhi* CECT 725, *Salmonella typhimurium* CECT 4594, *Escherichia coli* ETEC CECT 501, *Escherichia coli* ETEC CECT 515, *Escherichia coli* EPEC CECT 729 and *Escherichia coli* EPEC CECT 742. (A) inhibitory effects of the 1% and 4% non-neutralized *Lactobacillus rhamnosus* CNCM I-4036 supernatant at 17 h of culture time for the bacteria *Salmonella typhi* CECT 725. (B) inhibitory effects of the 1% and 4% non-neutralized *Lactobacillus rhamnosus* CNCM I-4036 supernatant at 24 h of culture time for the bacteria *Salmonella typhi* CECT 725. (C) inhibitory effects of the 1% and 4% neutralized *Lactobacillus rhamnosus* CNCM I-4036 supernatant at 24 h of culture time for the bacteria *Salmonella typhimurium* CECT 4594. (D) inhibitory effects of the 1% and 4% non-neutralized *Lactobacillus rhamnosus* CNCM I-4036 supernatant at 17 h of culture time for the bacteria *Escherichia coli* ETEC CECT 501. (E) inhibitory effects of the 1% and 4% non-neutralized *Lactobacillus rhamnosus* CNCM I-4036 supernatant at 24 h of culture time for the bacteria *Escherichia coli* ETEC CECT 501. (F) inhibitory effects of the 1% and 4% non-neutralized *Lactobacillus rhamnosus* CNCM I-4036 supernatant at 17 h of culture time for the bacteria *Escherichia coli* ETEC CECT 515. (G) inhibitory effects of the 1% and 4% non-neutralized *Lactobacillus rhamnosus* CNCM 1-4036 supernatant at 17 h of culture time for the bacteria Escherichia coli EPEC CECT 729. (H) inhibitory effects of the 1% and 4% neutralized *Lactobacillus rhamnosus* CNCM I-4036 supernatant at 24 h of culture time for the bacteria *Escherichia coli* EPEC CECT 742.
Figure 13:
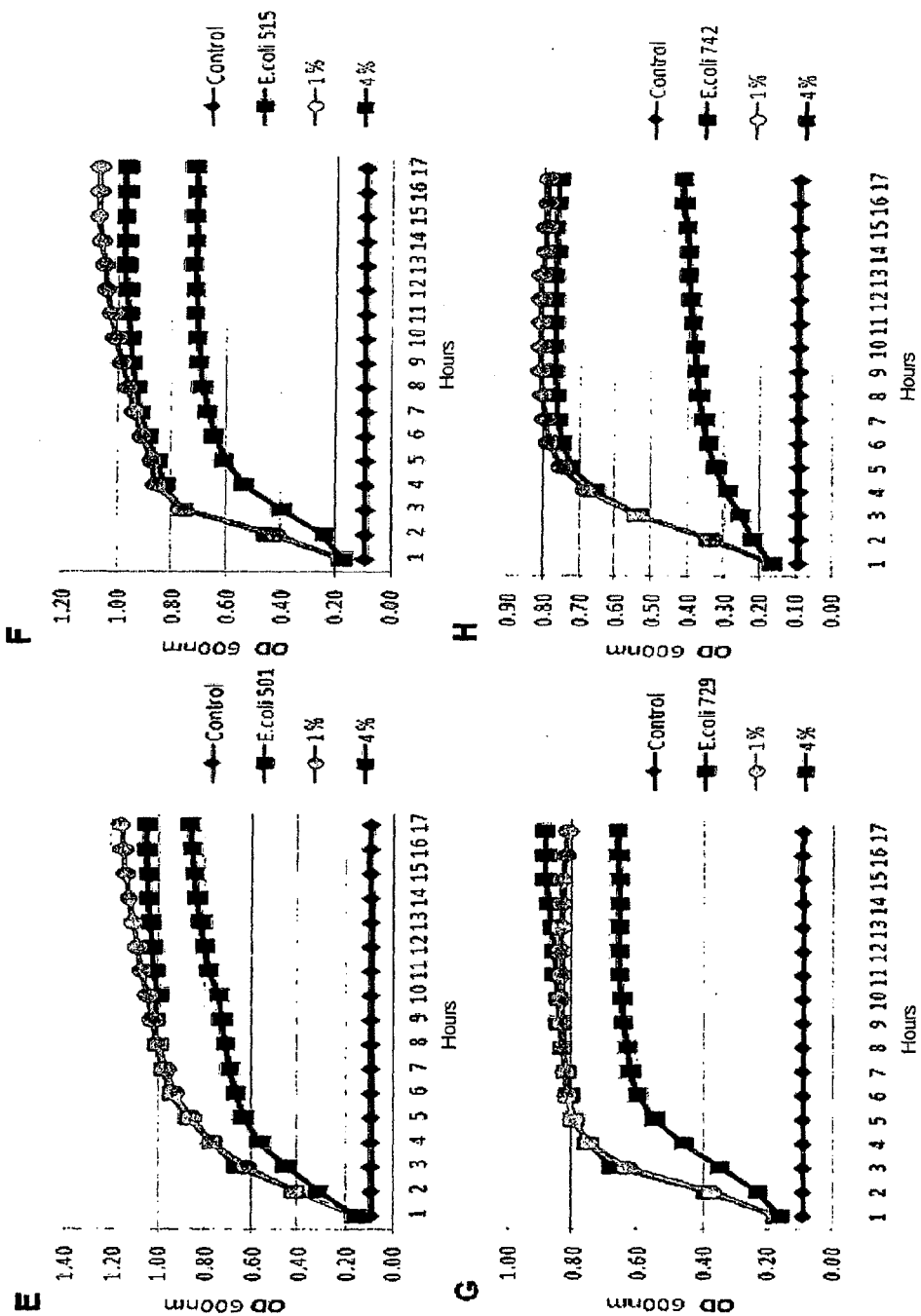

For the supernatant of the bacteria *L. rhamnosus* a significant growth inhibition mainly at 4% is seen for all the groups (*E coli* ETEC, *E. coli* EPEC and *Salmonella enterica*) (FIG. 13). This effect is mainly observed with the non-neutralized supernatant which again suggests that it is due to acid products derived from the fermentation, limiting the growth of the pathogen.

Although in the case of the *E. coli* EPEC (CECT 742) and *Salmonella typhimurium* (CECT 4594) inhibition is observed with the neutralized supernatant of 24 h, this effect can be attributed, as in the previous cases, to the presence of any type of factor or bacteriocin coming from the probiotic bacteria growth medium (FIG. 13).

Results of the Activity Assays in Liquid Medium with Respect to the Viral Digestive Pathogens: Human Rotavirus Ito, Wa and Va70

The infection protocols, detection of focus of infection and quantification of protective effect for the human rotavirus Ito, Wa and Va70 have been optimized. To obtain results which

TABLE 4 percentages of inhibition obtained for each of the pathogens in added culture media of supernatants of the study strains.

| | *L. paracasei* | | | | | | *L. rhamnosus* | | | | | | *B. breve* | | | | | |
|---|---|---|---|---|---|---|---|---|---|---|---|---|---|---|---|---|---|---|
| | 0.4% (v/v) | | 2% (v/v) | | 4% (v/v) | | 0.4% (v/v) | | 2% (v/v) | | 4% (v/v) | | 0.4% (v/v) | | 2% (v/v) | | 4% (v/v) | |
| | 17 h | 24 h | 17 h | 24 h | 17 h | 24 h | 17 h | 24 h | 17 h | 24 h | 17 h | 24 h | 17 h | 24 h | 17 h | 24 h | 17 h | 24 h |
| *L. monocytogenes* CECT 935 | 0.00 | 0.00 | 33.09 | 6.64 | 0.00 | 1.89 | 1.51 | 3.21 | 8.43 | 13.86 | 2.45 | 30.31 | 0.69 | 0.00 | 1.24 | 0.00 | 0.03 | 0.00 |
| *L. monocytogenes* CECT 4031 | 0.00 | 0.00 | 0.00 | 0.00 | 9.48 | 0.00 | 0.00 | 0.00 | 1.24 | 10.67 | 8.21 | 15.29 | 3.32 | 16.63 | 1.06 | 9.88 | 4.54 | 28.05 |
| *L. monocytogenes* CECT 911 | 2.60 | 5.73 | 7.31 | 9.92 | 25.64 | 16.81 | 8.46 | 5.18 | 11.99 | 18.36 | 15.53 | 28.13 | 4.22 | 0.00 | 0.00 | 0.00 | 0.00 | 0.00 |
| *S. sonnei* CECT 457 | 0.00 | 0.00 | 2.63 | 9.95 | 9.25 | 20.53 | 1.78 | 0.41 | 0.00 | 16.04 | 6.79 | 33.80 | 0.00 | 12.94 | 0.00 | 25.75 | 2.44 | 19.36 |
| *S. sonnei* CECT 413 | 28.72 | 0.00 | 32.51 | 3.88 | 80.99 | 82.10 | 0.00 | 5.17 | 5.49 | 16.32 | 80.95 | 82.06 | 8.05 | 0.00 | 7.19 | 0.00 | 14.83 | 0.00 |
| *S. sonnei* CECT 4887 | 0.00 | 0.00 | 2.63 | 9.95 | 9.25 | 20.53 | 0.00 | 0.00 | 0.00 | 10.05 | 3.80 | 29.07 | 0.00 | 0.00 | 0.00 | 0.00 | 0.00 | 0.00 |
| *H. pylori* LMG 4081$^T$ | 0.00 | 0.00 | 0.00 | 0.00 | 0.00 | 9.24 | 0.00 | 9.70 | 2.06 | 4.19 | 0.00 | 0.00 | 0.00 | 0.00 | 14.97 | 0.00 | 6.33 | 0.00 |
| *H. pylori* LMG 19499 | 21.15 | 13.34 | 51.70 | 41.05 | 75.80 | 70.89 | 17.36 | 36.67 | 54.84 | 61.13 | 83.48 | 85.28 | 12.56 | 37.80 | 37.79 | 71.92 | 57.33 | 77.56 |
| *H. pylori* LMG 8775 | 13.84 | 31.34 | 34.61 | 74.04 | 33.65 | 95.66 | 0.00 | 0.00 | 0.00 | 22.50 | 70.77 | 44.22 | 25.77 | 20.38 | 35.38 | 58.55 | 38.50 | 85.00 | are as representative as possible, the infection and protection assays have been carried out in the HT-29 human cell line.

Figure 14:
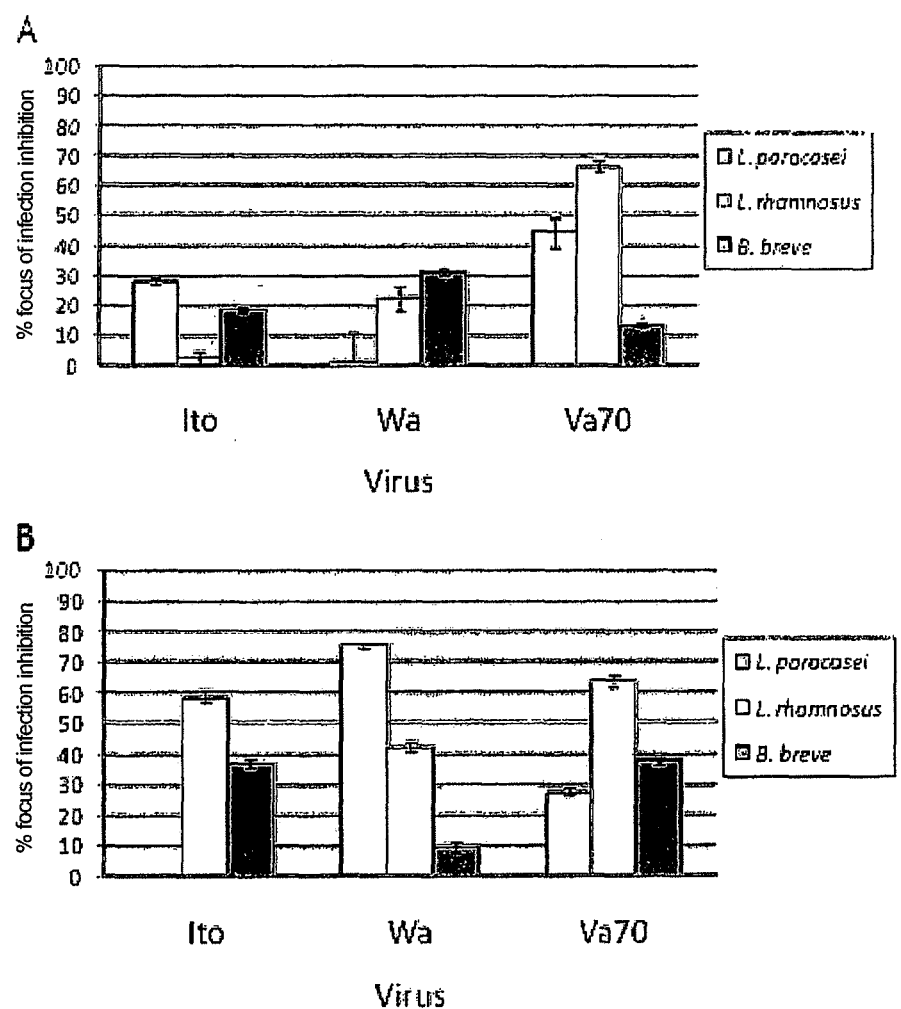
FIG. 14 shows the reduction of focus of infection obtained in the virus Ito, Wa and VA70 on the HT-29 line from supernatants concentrated 1× of the strains of the present invention after (A) 17 h of growth and (B) 24 h of growth.

Once the virus is amplified in MA-104 cells, they were titrated in the HT-29 line. The titers obtained in focus of infection forming units were $2.02 \times 10^6$ ffu/mL for the virus Ito, $6.80 \times 10^4$ ffu/mL for the virus Wa and $2.33 \times 10^5$ ffu/mL for the virus Va70. The virus were carried to the concentrations suitable for infection from the titration results obtained. To assure the correctness of the assays, the assays of infection were performed using three consecutive serial decimal dilutions and the assays were performed in triplicate. FIG. 14 summarizes the results of reduction of focus of infection obtained in supernatants without previously concentrating neutralized supernantants, coming from cultures of 24 h. These results indicate that the strains of the present invention reduce the focus of infection of all the virus tested (Wa, Ito and Va70).

Literature

Adolfsson O, Meydani S N, Russell R M. Yogurt and gut function. Am J Clin Nutr 2004; 80:245-256.

Agarwal B B, Shishodia S, Ashikawa K, Bharti AC. The role of TNF and its family members in inflammation and cancer: lessons from gene deletion. Curr Drug Targets Inflamm Allergy 202; 1 :327-41.

Akalin AS, Gonc S, Duzel S, Influence of yogurt and acidophilus yogurt on serum cholesterol levels in mice j Dairy Sci1997; 80:2721-25.

Andrighetto C, De Dea P, lombardi A, Neviani E, Rossetti L. Giraffa G. Molecular identification and cluster analysis of homofermentative thermophiliclactobacilli isolated from dairy products. Res Microbiol 1998; 149: 631-643.

Archer S Y, Meng S, Shei A, et al. P21 (WAFI) is required for butyrate-mediated growth inhibition of human colon cancer cells. Proc Nati Acad Sci USA 1998; 95:6791-96.

Arhne S, Molin G, Stahl S. Plasmids in Lactobacillus strain isolated from meat and meat products. Syst Appl Microbiol 1989; 11 :320-325.

Backhed F, Ley R E, Sonnenburg J L, et al. Host-bacterial mutualism in the human intestine. Science.2005; 307: 1915-1920.

Bai A P, Ouyang Q, Xiao X, Li S F. Probiotics modulate inflammatory cytokine secretion from inflammed mucosa in active ulcerative colitis. Int j Clin Pract 2006; 60:284-88.

Barry T, Colleran G, Glenon M, Dunican L, Gannon F. The 16S/23S ribosomal spacer as a target for DNA probes to identify eubacteria. PCR Methods Appl 1991 ; 1:51-56.

Beerens. Detección of bifidobacteria by using propionic acid as a selective agent. Appl Env Microbio 1991 ; 57:2418-19.

Berg R D. Probiotics, prebiotics or "conbiotics." Trends Microbiol 1998; 6:89-92.

Bernet M F, Brassart D, Neeser J R, Servin A L. Lactobacillus acidophilus LA-1 binds to cultured human intestinal cell-lines and inhibits cell attachment and cell invasion by enterovirulent bacteria. Gut 1994; 35:483-9.

Bezirtzoglou E. The intestinal microflora during the first weeks of life. Anaerobe 1997; 3:173-177.

Biller J A, Katz A F, Flores A F, Buie T M, Gorbach S L. Treatment of recurrent Clostridium difficile colitis with Lactobacillus GG. J Pediatr Gastroenterol Nutr. 1995; 21 :224-6.

Black F T, Andersen P L, Orskov J, et al. Prophylactic efficacy of lactobacilli on traveler's diarrhea. Travel Med 1989; 7: 333-5.

Botes M, Loos B, van Reenen C A. Adhesion fo the probiotics strains Enterococcus mundtii ST4SA and Lactobacillus plantarum 423 to Caco-2 cells under conditions simulating the intestinal tract, and in the presence of antibiotics and anti-inflammatory medicaments. Arch Microbiol 2008; 190: 573-584.

Botic, T., Klingberg, T. D., Weingartl, H., Cencic, A. (2007) A novel eukaryotic cell culture model to study antiviral activity of potential probiotic bacteria. International Journal of Food Microbiology. 115 (2): 227-234.

Bouton Y, Guyot P, Grappin R. Preliminary characterization of microflora of comte cheese. J Appl Microbiol 1998; 85:123-131.

Brownlee I A, Havler M E, Dettmar P W, Alien A, Pearson J P. Colonic mucus: secretion and turnover in relation to dietary fibre intake. Proc Nutr Soc 2003; 62:245-249.

Butler M, Ng C, van Heel D, Lombarda G, Lechler R, Playford R, Ghosh S. Modulation of dendritic cell phenotype and function in an in vitro model of the intestinal epithelium. Eur j Immunol 2006; 36:864-74.

Buts J P, De Keyser N. Effects of Saccharomyces boulardii on intestinal mucosa. Dig Dis Sci 2006; 51:1485-92.

Buts J P, DeKeyser N, Marandi S, Hermans D, Chae Y H E, Lambotte L, Chanteux H, Tulkens P M. Saccharomyces boulardii up-grades cellular adaptation after proximal enterectomy in rats. Gut 1999; 45:89-96.

Castagliuolo I, Riegler M F, Valenick L, LaMont J T, Pothoulakis C. Sacharomyces boulardii protease inhibits the effects of Clostridium difficile toxins A and B in human colonic mucosa. Infect Immu 1999; 67:302-7.

Cebeci A, Gurakan C. Properties of potential probiotic Lactobacillus plantarum strains. Food Microbiol 2003; 20:511-518.

Cetina-Sauri G, Sierra Basto G. Evaluation therapeutique de i Saccharomyces boulardii chez des enfants souffrant de diarrhee aigué. Ann Pediatr 1994 ; 41 :397-400.

Chai F, Evdokiou A, Young G P, et al. Involvement of p21 (Wafl/Cipl) and its cleavage by DEVD-caspase during apoptosis of colorectal cancer ccells induced by butyrate. Carcinogenesis 2000; 21:7-14.

Chu H, Kang S, Ha S. Cho K, Park S M, Han K H, et al. Lactobacillus acidophilus expressing recombinant K99 adhesive fimbriae has an inhibitory effect on adhesion of enterotoxigenic escherichia coli. Microbiol Immunol 2005; 49:941-8.

Clements M L, Levine M M, Black R E, Robins-Browne R M, Cisneros L A, Drusano G L, Lanata C F, Saah A J. Lactobacillus prophylaxis for diarrhea due to enterotoxigenic Escherichia coli. Antimicrob Agents Chemother. 1981 ; 20:104-8.

Coconnier M, Lievin V, Bernet-Camard M F, Hudault S, Servin A. Antibacterial effect of the adhering human Lactobacillus acidophilus strain L B. Antimicrob Agents Chemother 1997; 41 :1046-52.

Collins M, Samelis J, Metaxopoulos J, Wallbanks S. Taxonomic studies on some leuconostoc-like organims from fermented sausages: description of a new genus Weissella for the Leuconostoc paramesenteroides group of species. J Appl Bacteriol 1993; 75:595-603.

Coronen R, Korpela R, Moilanen E. Signalling mechanisms involved in the induction of inducible nitric oxide synthase by Lactobacillus rhamnosus GG, endotoxin, and lipoteichoic acid. Inflammation 2002; 26:207-14.

Cui H, Chen C L, Wang J D, Yang U J, Cun Y, Wu J B, Liu Y H, Dan H L, Jian Y T, Chen X Q. Effects of probiotic on intestinal mucosa of patients with ulcerative colitis. World j Gastroenterol 2004; 10:1521-25.

D'Souza A L, Rajkumar C, Cooke J, Bulpitt C J. Probiotics in prevention of antibiotic associated diarrhoea: meta-analysis. BMJ 2002; 324:1361.

Danielson A D, Peo E R Jr, Shahani K M, Lewis A J, Whalen P J, Amer M A. Anticholesteremic property of *Lactobacillus acidophilus* yogurt fed to mature boars. J Anim ScL 1989;67: 966-74.

De angelis M, Corsetti A, Tosti N, Rossi J, Corbo M, Gobbetti M. Characterization of non-starter lactic acid bacteria from Italian ewe cheese based on phenotypic, genotypic, and cell wall protein analyses. Appl Environ Microbiol 2001 ; 67:2010-20.

De Man J C, Rogosa M, Sharpe M T. A medium for the cultivation of lactobacilli. J Appl Bacteriol 1960; 23:130-5.

De Vrese M, Stegelmann A, Richter B, Fenselau S, Laue C, Schrezenmeir J. Probiotics-compensation for lactase insufficiency. Am J Clin Nutr. 2001 ; 73:421 S-429S.

Desjardins M L and Roy D. Growth of bifidobacteria and their enzyme profiles. J Dairy Sci 1990; 73:299-307.

Di Caro S, Tao H, Grillo A, EHa C, Gasbarrini G, Sepulveda A R, Gasbarrini A. Effects of *Lactobacillus GG* on genes expression pattern in small bowel mucosa. Dig Liver Dis 2005; 37:320-29.

Di Sabatino A, Ciccocioppo R, Luinetti O, et al. Increased enterocyte apoptosis in inflamed areas of Crohn's disease. Dis Colon Rectum 2003; 46:1498-1507.

Dunne C, Murphy L, Flynn S, O'Mahony L, O'Halloran S, Feeney M, Morrissey D, Thornton G, Fitzgerald G, Daly C, Kiely B, Quigley E M, O'Sullivan G C, Shanahan F, Collins J K. Probiotics: from myth to reality. Demonstration of functionality in animal models of disease and in human clinical trials. Antonie Van Leeuwenhoek. 1999; 76:279-92.

Dunne C, O'Mahony L, Murphy L, Thornton G, Morrissey D, O'Halloran S, Feeney M, Flynn S, Fitzgerald G, Daly C, Kiely B, O'Sullivan GC, Shanahan F, Collins J K. In vitro selection criteria for probiotico bacteria of human origin: correlation with in vivo findings. Am J clin Nutr 2001 ; 73 (suppl) 386S-92S.

Eaden J A, Abrams K R, Matberry J F. The risk of colorectal cancer in ulcerative colitis: a meta-analysis. Gut 2001; 48:526-535.

Fabia R, Ar'Rajab A, Johansson M, Andersson R, Willen R, Jeppsson B, Molin G, Bengmark S. Impairment of bacterial flora in human ulcerative colitis and experimental colitis in the rat Digestion 1993; 54:248-255.

FAOANHO (2002). Report of a Joint FAO/WHO Working Group on Drafting Guidelines for the Evaluation of Probiotics in Food.

Favier C, Neut C, Mizon C, Cortot A, Colombel J, Mizon j. Fecal beta-D-galactosidase production and Bifidobacteria are decreased in Crohn's disease. Dig Dis Sci 1997; 42:817-822.

Floch M H, Binder H J, Filburn B, Gershengoren W. The effect of bile acids on intestinal micromicrobiota. Am J Clin Nutr 1972; 25:1418-26.

Forestier C, de Champs C, Valtoux C, Joly B. Probiotic activities of *Lactobacillus casei* rhamnosus: in vitro adherence to intestinal cells and antimicrobial properties. Res microbiol 2001; 152:167-173

Fukushima M, Nakano M. Effect of a mixture of organisms, *Lactobacillus acidophilus* or *Streptococcus faecalis* on cholesterol metabolism in rats fed on a fat- and cholesterol-enriched diet. Br j Nutr 1996; 76:857-67.

Fuller R. Probiotics in man and animals. J Appl Bacteriol. 1989; 66:365-78.

Fuller R., ed. Probiotics: the scientific basis. London: Chapman & Hall, 1992

Gilliland S E, Nelson C R, Maxwell C. Assimilation of cholesterol by *Lactobacillus acidophilus*. Appl Environ Microbiol. 1985; 49:377-81.

Goldin B R, Gorbach S L. Probiotics for humans. In: Fuller R, ed. Probiotics, the scientific basis. London: Chapman and Hall, 1992;355-76.

Gopal P, Sullivan P, Smart J. Utilisation of galacto-oligosaccharides as selective substrate for growth by lactic acid bacteria including *Bifidobacterium lactis* DR 10 and *Lactobacillus acidophilus* DR 20. lnt Dairy J 2001; 11:19-25.

Gopal PK, Prasad J, Smart J, Gill H S. In vitro adherence properties of *Lactobacillus rhamnosus* DR20 and *Bifidobacterium lactis* DR10 strain and their antagonistic activity against an eterotoxigenic *Escherichia coli*. lnt J Food Microbiol 2001 ; 67:207-16.

Gorbach S L, Chang T W, Goldin B. Successful treatment of relapsing Clostridium difficile colitis with *Lactobacillus GG*. Lancet. 1987; 2:1519.

Gordon J I, Hooper L V, McNevin M S, Wong M, Bry L. Epithelial cell growth and differentiation.111. promoting diversity in the intestine: conversations between the microflora, epithelium, and diffuse GALT. Am J Physiol Gastrointest Liver Physiol 1997; 273:G565-G70.

Gotz V, Romankiewicz J A, Moss J, Murray H W. Prophylaxis against ampicillin-associated diarrhea with a *lactobacillus* preparation. Am J Hosp Pharm. 1979; 36:754-7.

Grupa P, Andrew H, Kirschner B S, et al. Is *Lactobacillus GG* helpful in children with Crohn's disease? Results of preliminary, open-label study. J Pediatr Gastroenterol Nutr 2000; 31:453-457.

Gulewicz P, Szymaniec S, Bubak B, Frias J, Vidal-Valverde C, Trajanowska K, Gulewicz K. Biological activity of a-galactoside preparations from Lupinus angustifolius L and *Pisum sativum* L seeds. J Agr food chem 2002; 50:384-389.

Harms H K, Bertele-Harms R M, Bruer-Kleis D. Enzyme-substitution therapy with the yeast *Saccharomyces cerevisiae* in congenital sucrase-isomaltase deficiency. N Engl J Med. 1987 ;316:1306-9.

Harmsen H J, Wildeboer-Veloo A C, Raangs G C, Wagendorp A A, Klijn N, Bindels J G, Welling G W. Analysis of intestinal flora development in breast-fed and formula-fed infants by using molecular identification and detection methods. J Pediatr Gastroenterol Nutr 2000; 30:61-67.

Heerdt B G, Houston M A, Augenlicht L H. Short-chain fatty acid-initiated cell cycle arrest and apoptosis of colonic epithelial cells is linked to mitochondrial function. Cell Growth Differ 1997; 8:523-532.

Heiling H G, Zoetendal E G, Vaughan E E, Marteu P, Akkermans A D, and de Vos W M. Molecular diversity of *Lactobacillus* spp. And other lactic acid bacteria in the human intestine as determined by specific amplification of 16S ribosomal DNA. Appl Environ Microbiol 2002; 68:114-123.

Henriksson A, Khaled A K D, P L Conway. *Lactobacillus* colonization of the gastrointestinal tract of mice after removal of the non secreting stomach region. Microb Ecol Health Dis 1999; 11 :96-9.

Hilton E, Kolakowski P, Singer C, Smith M. Efficacy of *Lactobacillus* GG as a Diarrheal Preventive in Travelers. J Travel Med. 1997; 4:41-43.

Höchter W, Chase D, Hegenhoff G. *Saccharomyces boulardii* in treatment of acute adult diarrhea. Efficacy and tolerance of treatment. Munch Med Wochen 1990; 132: 188-92.

Holzapfel, W. H., Haberer, P., Snel, J., Schillinger, U., Huisin't Veld, J. H. J., Overview of gutflora and probiotics. International Journal of Food Microbiology 1998; 41, 85-101.

Hopkins M, Cummings H, McFarlane G. Interspecies differences in maximum specific growth rates and cell yields of bifidobacteria cultured on oligosaccharides and other simple carbohydrate source. J Appl Microbiol 1998; 85:381-386.

Isolauri E, Salminen S,. Probiotics, gut inflammation and barrier function. Gastroentero Clin North Am 2005; 34:437-450.

Iwamoto M, Koji T, Makiyama K, et al. Apoptosis of crypt epithelial cells in ulcerative colitis. J Pathol 1996; 180: 152-159.

Jack R W, Tagg J R, Ray B. Bacteriocins of gram positive bacteria. Microbiol Rev 1995; 59:171-200.

Jankowska A, Laubitz D, Antushevich H, Zabielski R, Grzesiuk E. Competition of *Lactobacillus paracasei* with *Salmonella enterica* for adhesion to Caco-2 cells. J Biomed Biotechnol 2008; 2008:357964.

Jin L Z, Ho W Y, Abdullah N, Jalaludin S. Acid and bile tolerance of *Lactobacillus* isolated from chicken intestine. Lett. Appl. Microbiol. 1998; 27:183-185.

Jobin C, sartor R B,. The IkB/NF-kB system: a key determinat of mucosal inflammation and protection. Am J Physiol Cell Physiol 2000; 278:C451-C462.

Julia M, Wong R D, Russell de Souza R D, Cyril W, et al. Colonia health: fermantation and short Chain fatty acids. J Clin Gastroenterol 2006; 40:235-243.

Kalliomaki M A, lsolauri E. Probiotics and down-regulation of the allergic response.lmmunol Allergy Clin North Am 2004; 24:739-752.

Kelsall B, Biron C, Sharma O, Kaye P. Dendritic cells at the host-pathogen interface.Nat immunol 2002; 3:699-702.

Klaenhammer T R. Genetics of bacteriocins produced by acid lactic bacteria. FEMS Microbiol Rev 1993; 12:39-85.

Ko J S, Yang H R, Chang J Y, Seo J K. *Lactobacillus plantarum* inhibits epithelial barrier dysfunction and interleukin-8 secretion induced by tumor necrosis factor-a. World J Gastroenterol 2007; 13:1962-65.

Kollaritsch H, Holst H, Grobara P, et al. Prophylaxe der reisediarrhoe mith *Saccharomyces boulardii*. Forst Chr Med 1993; 111:152-56.

Koshiji M, Adachi Y, Sogo S. Apoptosis of colorectal adenocarcinoma (COLO201) by tumour necrosis factor alpha (TNF-alpha) and/or interferon-gamma(IFN-gamma), resulting from down-regulation of Bcl-2 expression. Clin Exp Immunol 1998; 1 11:211-218.

Kulkami N, Zang E, Kelloff G. Effect of the chemopreventive agents piroxicam and D,L-alpha-difluoromethylomithine on intermediate biomarkers of colon carcinogenesis. Carcinogenesis 1992; 13:995-1000.

Kurmann J. Started for fermented milk: Started with selected intestinal bacteria. Bull Int Dairy Fed 1988; 227:41-45.

Lee Y-K, Salminen S. The coming age of probiotics. Trends Food Sci Technol 1995; 6:241-5.

Lee, Y. K., Puong, K. Y., Ouwehand, A. C, Salminen, S., Displacement of bacterial pathogens from mucus and Caco-2 cell surface by lactobacilli J Med Microbio 2003; 52:925-930.

Lewis R, Gorbach S. Modificaron of bile acids by intestinal bacteria.Arch Intern Med 1972; 130:545-9.

Lin M Y, Yen C L, Chen S H. Management of lactose maldigestion by consuming milk containing lactobacilli. Dig Dis Sci. 1998; 43:133-7.

Lin S Y, Ayres J W, Winkler W, Sandine W E. *Lactobacillus* effects on cholesterol: in vitro and in vivo results. J Dairy Res 1989; 72:885-9.

Madsen K, Cornish A, Soper P, et al. Probiotic bacteria enhance murine and human intestinal epithelial barrier function. Gatroenterology 2001; 121:580-591.

Mahé S, Marteau P, Huneau JF, Thuillier F, Tome D. Intestinal nitrogen and electrolyte movements following fermented milk ingestion in man. Br J Nutr. 1994; 71:169-80.

Makras L, Van Acker G, De Vuyst L. *Lactobacillus paracasei* subsp. Paracasei 8700:2 degrades inulin-type fructans exhibiting different degrees of polymerization. Appl Enviro Microbiol 2005; 71:6531-6537.

Marini M, Bamias G, Rivera-Nieves J. TNF-D neutralization ameliorates the severity of murine Crohn's-like ileitis by abrogation of intestinal epithelial cell apoptosis. Proc Nati Acad Sci USA 2003; 100:8366-8371.

Marteau P, Flourie B, Pochart P, Chastang C, Desjeux J F, Rambaud JC. Effect of the microbial lactase (EC 3.2.1.23) activity in yoghurt on the intestinal absorption of lactose: an in vivo study in lactase-deficient humans. Br J Nutr. 1990; 64:71-9.

McFarland L V, Surawicz C M, Greenberg R N, et al. Prevention de β-lactam associated diarrhea by *Saccharomyces boulardii* compared with placebo. Am J Gastroenterol 1995; 90:439-48.

Medina R, Katz M, Gonzalez S, Oliver G. Characterization of the lactic acid bacteria in ewe's milk and cheese from northwest Argentina. J Food Prot 2001; 64:559-563.

Medina V, Edmonds B, Young G, James R, Appleton S, Zalewski P. Induction of caspase-3 protease activity and apoptosis by butyrate and trichostatin A (inhibitors of histone deacetylase):Dependence on protein synthesis and synergy with a mitochondrial/cytochrome c-dependent patway. 1997; 57:3697-3707.

Metchnikoff E. Etudes sur la flore intestinale. Ann. Inst. Pasteur Paris 1908; 22:929-55.

Morata De Ambrosini, Ganzalez, S. N., Oliver, G. Study of adhesion of *Lactobacillus casei* CRL431 to ileal intestinal cells of mice. J. Food Prot.1999; 1430-1434.

Nanno M, Morotomi M, Takayama H, Kuroshima T, Tanaka R, Mutai M. Mutagenic activation of biliary metabolites of benzo(a)pyrene by b-glucoronidase-positive bacteria in human faeces. J Med Microbiol 1986; 22:351.

Navarro E, Simonet P, Normard P, Bardin R. Characterization of natural populations of Nitrobacter spp. using PCR/RFLP analyses of the ribosomal intergenic spacer. Arch Microbiol 1992; 157:107-115.

Nebra Y, Blanch A R. A new selective medium for *Bifidobacterium* spp. Appl Environ Microbiol. 1999; 65:5173-6.

Niedergang F, Kweon M. New trends in antigen uptake in the gut mucosa. Trends Microbiol 2005; 13:485-90.

O'Hara A, O'Regan P, Fanning A, O'Mahony C, MacSharry J, Lyons A, Bienenstock J, O'mahony L, Sanan F. Functional modulation of human intestinal epithelial cell responses by *Bifidobacterium* inf antis and *Lactobacillus salivarius*. Immunology 2006; 118:202-15.

Otles S, Cagindi O & Akcicek E Probiotics and health. Asian Pac J Cancer Prey 2003; 4:369-372.

Ouwehand, A C., Kirjavainen, P. V., Shortt, C., Salminen, S. Probiotics: mechanisms and establishe deffects. intern Dairy J 1999; 9:43-52.

Percy-Robb I W, Collee J G. Bile acids: a pH dependent antibacterial system in the gut? Br Med J 1972; 3:813-5.

Piaia M, Antoine J M, Mateos-Guardia J A, Lepligard A, Lenoir-Wijnkoop I. Assessment of the benefits of live yogurt methods and markers for in vivo studies of the physiological effects of yogurt cultures. Microb Ecol Health Dis 2003; 15:79-87.

Pickard K M, Bremner A R, Gordon J N, et al. Microbial-gut interactions in health and disease. Immune responses. Best Pract Res Clin Gastroenterol. 2004; 18:271-285.

Plant, L J. , Conway, P. L.,2002. Adjuvant properties and coloniza-tion potential of adhering and non-adhering *Lactobacillus* spp. Following oral administration to mice. FEMS Immunol Med Microbio 2002; 34:105-111.

Ratajczak C, Duez C, Grangette C, Pochard P, Tonnel A B, Pestel J. Impact of lactic acid bacteria on dendritic cells from allergic patients in an experimental model of intestinal epithelium. J Biomed Biotechnol 2007; 1:719-21.

Riedel C, Foata F, Philippe D, Adolfsson O, Eikmanns B, Blum S.Anti-inflammatory effects of bifidobacteria by inhibition of LPS-induced NF-kB activation. World J Gastroenterol 2006; 12:3729-35.

Rimoldi M, Chieppa M, Salucci V, Avogadri F, Sonzogni A, Sampietro G, NespoliA, Viale G, Allavena P, Rescigno M. Intestinal immune homeostasis is regulated by the crosstalk between epithelial cells and dendritic cells. Nat immunol 2005; 6:507-14.

Rioux K P, Fedorak R N. Probiotics in the treatment of inflammatory bowel disease. J Clin Gastroenterol 2006; 40:260-263.

Roberfroid M, Van Loo E, Gibson R. The bifidogenic nature of chicory inulin and its hydrolysis products, J Nutr 1998; 128:11-19.

Ross RP, Desmond C, Fitzgerald GF, Staton C . Overcoming the technological hurdles in the development of probiotic food. J. Appl. Microbiol. 2005; 98:1410-17.

Sablón E, Contreras B, Vandamme E. Antimicrobial peptide of lactic acid bacteria: mode of action, genetics and biosynthesis. Adv Biochem Eng Biotechnol 2000; 68:21-60.:

Satokari R M, Vaughan E E, Favier C, Dore J, Edwards C, and de Vos W M. Diversity of *Bifidobacterium* and *Lactobacillus* spp. in breast-fed and formula-fed infants as assessed by 16S rDNA sequence differences. Microbiol Ecol Health Dis 2002; 14:97-105.

Savage DC. Microbial ecology of the gastrointestinal tract. Annu Rev Microbiol 1977 31; 31 :107-33.

Senmeir J, deVrese M. Probiotics, prebiotics, and Synbiotics, approaching a definition. Am J Clin Nutr 2001; 73:361 S-64S.

Servin A. Antagonistic activities of lactobacilli and bifidobacteria against microbial pathogens. FEMS Microbiol Rev 2004; 28:405-440.

Siitonen S, Vapaatalo H, Salminen S, Gordin A, Saxelin M, Wikberg R, Kirkkola A L. Effect of *Lactobacillus* GG yoghurt in prevention of antibiotic associated diarrhea. Ann Med. 1990; 22:57-9.

SilvaM, Jacobs N V, Deneke C, Gorbach S L. Antimicrobial substance fro a human *Lactobacillus* strain: Antimicrob Agents Chemother. 1987; 31 :1231-33.

Sing J, Rvenson A, Tomita M, Shimamura S, lshibashi N, Reddy B. *Bifidobacterium longum*, a lactic acid-producing intestinal bacterium inhibits colon cancer and modulates the intermediate biomarkers of colon carcinogenesis. Carcinogenesis 1997; 18:833-41.

Sinocrope FA, Roddey G, Mc Donnell T J. Increased apoptosis accompanies neoplastic development in the human colorectum. Clin Cancer Res 1996; 2:1999-2006.

Snelling AM Effects of probiotics on the gastrointestinal tract. Curr Opin Infeci Dis 2005; 18:420-4126.

Spinler, J. K., Taweechotipatr, M., Rognerud, C. L., Oub, C. N., Tumwasorn, S., Versalovic, J. (2008) Human-derived probiotic *Lactobacillus reuteri* demonstrate antimicrobial activities targeting diverse enteric bacterial pathogens. Anaerobe 14: 166-171.

Steiner T S, Nataro J P, Poteet-Smith C E, Smith J A, Guerrant R L. Enteroaggregative *Escherichia coli* expresses a novel flagellin that causes IL-8 release from intestinal epithelial cells. J Clin Invest 2000; 105:1769-77.

Stewart L, Pellegrini C A, Way L W. Antibacterial activity of bile acids against common biliary tract organisms. Surg Forum 1986; 37:157-9.

Surawicz C M, Elmer G W, Speelman P, McFarland L V, Chinn J, Van Belle G. Prevention of antibiotic associated diarrhoea by *Saccharomyces boulardii*: Aprospective study. Gastroenterology 1989; 96:981-88.

Taranto M P, Medici M, Perdigón G, Ruiz Holgado A P, Valdez G F. Evidence for hypocholesterolemic effect of *Lactobacillus reuteri* in hypercholesterolemic mice. J Dairy Sci. 1998; 81 :2336-40.

Thornton GM. Probiotic bacteria. Selection of *Lactobacillus* and *Bifidobacterium* strains from the healthy human gastrointestinal tract; characterization of a novel *Lactobacillus*-derived antibacterial protein. PhD thesis. National University of Ireland, Cork, Ireland, 1996.

Tien M T, Girardin S, Regnault B, Le Bourhis L, Dillies M, Coppée J Y, Bourdet-Sicard R, Sansonetti P, Pédron T. Anti-Inflammatory effect of *Lactobacillus casei* on *Shigella*-Infected Human Intestinal Epithelial Cells. J Immunol 2006; 176:1228-37.

Todoriki K, Mukai T, Sato S, Toba T. Inhibition of adhesion of food-borne pathogens o Caco-2 cells by *Lactobacillus* strains. J Appl Microbiol 2001 ; 91:154-9.

Tsai C, Lin P, Hsieh Y. Three *Lactobacillus* strains from healthy infant stool inhibit enterotoxigenic *Escherichia coli* grown in vitro. Anaerobe 2008; 14:61-7.

Tuomola E M, Salminen S J. Adhesion of some probiotic and dairy *Lactobacillus* strains to Caco-2 cell cultures, Int J Food Microbiol 1998; 41 : 45-51

Van Loo J, Cummings J, Delzenne N, Englyst H, Franck A, Hopkins M, Kok N, Macfarlane G, Newton D, Quigley M, Roberfroid M. Functional food properties of nondigestibles oligosaccharides a consensus report from the ENDO project (DGXII Al- RII-CT94-1095) Br J Nutr 1999; 81 :121-132.

Vanderhoof J A, Whitney D B, Antonson D L, Hanner T L, Lupo J V, Young R J. *Lactobacillus* GG in the prevention of antibiotic-associated diarrhea in children. J Pediatr. 1999; 135:564-8. i Wallace T, Bradley S, Buckley N, Green-Johnson J M. Interactions of lactic acid bacteria with human intestinal epithelial cells: effects on cytokine production. J food Protect 2003; 66:466-72.

Wang S, Ng L, Chow W L, Lee Y K. Infant intestinal enterococcus faecalis down-regulates inflammatory responses in human intestinal cell lines. World J Gastroenterol 2008; 14:1067-76.

Weitzman S A, Gordon L I. Inflammation and cancer: role of phagocyte-generated oxidants in carcinogenesis. Blood 1990; 76:655-66.

Wunderlich P F, Braun L, Fumagalli I, D'Apuzzo V, Heim F, Karly M, Lodi R, Politta G, Vonbank F, Zeltner L. Double-blind report on the efficacy of lactic acid-producing *Enterococcus* SF68 in the prevention of antibiotic-associated diarrhoea and in the treatment of acute diarrhoea. J Int Med Res. 1989; 17:333-8.

Yan F, Polk D. Probiotic bacterium prevents cytokine-induced apoptosis; in intestinal epithelial cells. J Biolog Chem 2002; 277:50959-50965.

Zhang L, Li N, Caicedo R, Neu J. Alive and dead *Lactobacillus rhamnosus* GG decrease tumor necrosis factor-α-induced interleukin-8 production in Caco-2 cells. J Nutr 2005; 135:1752-56.

The invention claimed is:

1. An isolated strain of probiotic microorganism isolated from faeces of children exclusively fed with breast milk, wherein said strain is *Lactobacillus rhamnosus* HERO 22A (CNCM I-4036).

2. The strain of claim 1, wherein said strain is in the form of a pure biological culture.

3. The strain of claim 1, wherein said strain is in the form of viable cells.

4. The strain of claim 1, wherein said strain is in the form of non-viable cells.

5. A formulation comprising the strain of claim 1 and a carrier.

6. The formulation according to claim 5, wherein said formulation further comprises a strain selected from the group consisting of *Lactobacillus paracasei* HERO 7 (CNCM I-4034) and *Bifidobacterium breve* HERO 15B (CNCM I-4035).

7. The formulation according to claim 5, wherein said formulation further comprises another probiotic material.

8. The formulation according to claim 5, wherein said formulation further comprises prebiotic material.

9. The formulation according to claim 5, wherein said formulation further comprises a carrier suitable for the ingestion thereof.

10. The formulation according to claim 9, wherein said carrier is a pharmaceutically acceptable carrier selected from the group consisting of capsules, tablets and powders.

11. The formulation according to claim 10, wherein said food product is selected from the group consisting of milk; fermented milk and cheeses; cereals; bread doughs; soups; dehydrated food products; fermented meat products; fruit derivatives; juices and soft drinks.

12. The formulation according to claim 9, wherein said carrier is a food product.

13. The strain according to claim 1, wherein said strain is present in infant formula milk.

14. The strain according to claim 1, wherein said strain is present in a food product selected from the group consisting of ready-to-eat infant milk, infant cereals, and infant foods.

15. The strain according to claim 1, wherein said strain is present in a food supplement.

16. The strain according to claim 1, wherein said strain is present in a formulation for oral and/or enteral nutrition.

17. The strain according to claim 1, wherein said strain is present in a pharmaceutical product.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n = A or C

<400> SEQUENCE: 1
agagtttgat cntggctcag                                                   20

<210> SEQ ID NO 2
<211> LENGTH: 22
<212> TYPE: DNA
<213> ORGANISM: Artificial Sequence
<220> FEATURE:
<223> OTHER INFORMATION: Synthetic oilgonucleotide
<220> FEATURE:
<221> NAME/KEY: misc_feature
<222> LOCATION: (6)..(6)
<223> OTHER INFORMATION: n = C or T

<400> SEQUENCE: 2
tacggntacc ttgttacgac tt                                                22

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (9)..(9)
<223> OTHER INFORMATION: n = A or G
<220> FEATURE:
<221> NAME/KEY: misc_feature
<222> LOCATION: (10)..(10)
<223> OTHER INFORMATION: n = A or T
<220> FEATURE:
<221> NAME/KEY: misc_feature
<222> LOCATION: (11)..(11)
<223> OTHER INFORMATION: n = C or T
<220> FEATURE:
<221> NAME/KEY: misc_feature
<222> LOCATION: (19)..(19)
<223> OTHER INFORMATION: n = A or G

<400> SEQUENCE: 3
tggctcagnn ngaacgctng                                                   20

```
<210> SEQ ID NO 4
<211> LENGTH: 17
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (12)..(12)
<223> OTHER INFORMATION: n = A or T
<220> FEATURE:
<221> NAME/KEY: misc_feature
<222> LOCATION: (15)..(15)
<223> OTHER INFORMATION: n = A or G

<400> SEQUENCE: 4
gacgggcggt gngtnca                                                 17

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
ctcgtaggcg gttcgtcg                                                18

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 6
aacgggcccc acatccag                                                18

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
acaccgcccg tcacaccatg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: n = A or T
<220> FEATURE:
<221> NAME/KEY: misc_feature
<222> LOCATION: (4)..(4)
<223> OTHER INFORMATION: n = G or C

<400> SEQUENCE: 8
ccnnttcgct cgccgctact                                              20

<210> SEQ ID NO 9
<211> LENGTH: 21
```

```
<212> TYPE: DNA
<213> ORGANISM: Artificial Sequence
<220> FEATURE:
<223> OTHER INFORMATION: Synthetic oligonucleotide

<400> SEQUENCE: 9
gggatgctgg tgtggaagag a                                          21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
tgctcgcgtc cactatccag t                                          21
```